(12) United States Patent
Yamaguchi et al.

(10) Patent No.: US 12,281,187 B2
(45) Date of Patent: Apr. 22, 2025

(54) MICROWELL FILM FOR BIOASSAY, PHOTOSENSITIVE RESIN COMPOSITION FOR FORMATION OF THE MICROWELL FILM FOR BIOASSAY, AND METHOD OF MANUFACTURING THE MICROWELL FILM FOR BIOASSAY

(71) Applicant: ASAHI KASEI KABUSHIKI KAISHA, Tokyo (JP)

(72) Inventors: Fujito Yamaguchi, Tokyo (JP); Ryuichi Ito, Tokyo (JP); Makoto Okada, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 667 days.

(21) Appl. No.: 17/624,050

(22) PCT Filed: Jul. 1, 2020

(86) PCT No.: PCT/JP2020/025838
§ 371 (c)(1),
(2) Date: Dec. 30, 2021

(87) PCT Pub. No.: WO2021/002388
PCT Pub. Date: Jan. 7, 2021

(65) Prior Publication Data
US 2022/0340700 A1    Oct. 27, 2022

(30) Foreign Application Priority Data
Jul. 2, 2019    (JP) .................................. 2019-123981

(51) Int. Cl.
*C08F 220/24*    (2006.01)
*B32B 27/00*    (2006.01)
(Continued)

(52) U.S. Cl.
CPC ........ *C08F 220/24* (2013.01); *C08F 290/067* (2013.01); *C08J 5/18* (2013.01);
(Continued)

(58) Field of Classification Search
CPC ......... B32B 27/35; B32B 27/40; B32B 27/30; B32B 2038/0076; B32B 7/023; B32B 3/30; C08F 290/00; C12M 1/00
See application file for complete search history.

(56) References Cited

U.S. PATENT DOCUMENTS 6,818,436 B2 * 11/2004 Yamamoto .......... H01L 23/3677
257/E23.105
9,391,236 B2 * 7/2016 Yamaguchi ............ B82Y 40/00
(Continued)

FOREIGN PATENT DOCUMENTS

EP    1 691 196 A1    8/2006
JP    2003-70456 A    3/2003
(Continued)

OTHER PUBLICATIONS

Supplementary European Search Report for corresponding European Application No. 20834785.6, dated Aug. 8, 2022.
(Continued)

*Primary Examiner* — Rip A Lee
(74) *Attorney, Agent, or Firm* — Birch, Stewart, Kolasch & Birch, LLP

(57) ABSTRACT

To provide microwell films for bioassay suitable for a "unimolecular enzyme assay" method and methods of manufacturing the films, a microwell film for bioassay is comprised of at least a substrate (11), and a resin layer (12) having microwells on its surface provided on one main surface of the substrate (11), where in the substrate (11) and
(Continued)

the resin forming the resin layer (12), an absorption coefficient at each of wavelengths of 350 nm to 800 nm is 0.01 $\mu m^{-1}$ or less.

15 Claims, 3 Drawing Sheets

(51) Int. Cl.
*C08F 290/06* (2006.01)
*C08J 5/18* (2006.01)
*C09D 4/06* (2006.01)
*C12M 1/00* (2006.01)
*G03F 7/027* (2006.01)
*B32B 27/30* (2006.01)
*B32B 27/40* (2006.01)

(52) U.S. Cl.
CPC ............... *C09D 4/06* (2013.01); *G03F 7/027* (2013.01); *B32B 27/30* (2013.01); *B32B 27/40* (2013.01); *C08J 2325/06* (2013.01); *C08J 2345/00* (2013.01); *C08J 2367/02* (2013.01); *C08J 2369/00* (2013.01); *C08J 2383/04* (2013.01); *C12M 1/00* (2013.01)

(56) References Cited

U.S. PATENT DOCUMENTS

| | | | | |
|---|---|---|---|---|
| 10,642,176 | B2* | 5/2020 | Ha | G03G 5/14769 |
| 10,766,169 | B2* | 9/2020 | Matsumoto | B29C 33/58 |
| 11,883,999 | B2* | 1/2024 | Nakahara | C08L 75/16 |
| 2003/0047761 | A1 | 3/2003 | Yamamoto et al. | |
| 2005/0202163 | A1 | 9/2005 | Nguyen et al. | |
| 2007/0259381 | A1 | 11/2007 | Rissin et al. | |
| 2013/0004967 | A1 | 1/2013 | Halverson et al. | |
| 2013/0049255 | A1 | 2/2013 | Matsumoto et al. | |
| 2016/0243734 | A1 | 8/2016 | Pitzek et al. | |
| 2017/0097345 | A1 | 4/2017 | Oo et al. | |
| 2018/0202934 | A1* | 7/2018 | Sakurada | G01N 21/6428 |

FOREIGN PATENT DOCUMENTS

| | | | | |
|---|---|---|---|---|
| JP | 2004-309405 A | | 11/2004 | |
| JP | 2005-134339 A | * | 5/2005 | ............. G01N 21/03 |
| JP | 2005249429 A | * | 9/2005 | ............. G01N 33/53 |
| JP | 2008-44283 A | | 2/2008 | |
| JP | 2011-137830 A | | 7/2011 | |
| JP | 2013-19707 A | | 1/2013 | |
| JP | 2013-28006 A | | 2/2013 | |
| JP | 2014-58667 A | | 4/2014 | |
| JP | 2014123077 A | * | 7/2014 | ............... G02B 1/11 |
| JP | 2014229558 A | * | 12/2014 | ............ H05B 33/02 |
| JP | 2018-102159 A | | 7/2018 | |
| JP | 2018-529968 A | | 10/2018 | |
| JP | 2019-15610 A | | 1/2019 | |
| TW | 200531835 A | | 10/2005 | |
| WO | WO 2010/045357 A2 | | 4/2010 | |
| WO | WO 2011/111741 A1 | | 9/2011 | |

OTHER PUBLICATIONS

International Search Report (PCT/ISA/210) issued in PCT/JP2020/025838 mailed on Sep. 15, 2020.

Written Opinion (PCT/ISA/237) issued in PCT/JP2020/025838 mailed on Sep. 15, 2020.

"Anti-Fingerprint Agent OPTOOL DAC-HP (Additive)," Daikin, 2014, 6 pages total, with an English translation.

* cited by examiner

MICROWELL FILM FOR BIOASSAY, PHOTOSENSITIVE RESIN COMPOSITION FOR FORMATION OF THE MICROWELL FILM FOR BIOASSAY, AND METHOD OF MANUFACTURING THE MICROWELL FILM FOR BIOASSAY

TECHNICAL FIELD

The present invention relates to a microwell film for bioassay, photosensitive resin composition for formation of the microwell film for bioassay, and method of manufacturing the microwell film for bioassay using the resin composition.

BACKGROUND ART

For diagnoses of diseases, infections and the like, as techniques for promptly detecting markers of nucleic acid, protein, virus, cell and so on with high sensitivity, there is a "unimolecular enzyme assay" method of encapsulating a detection target substance such as nucleic acid, protein, virus and cell in liquid with minute capacity, and detecting by immunological technique using a labelled antibody. According to this method, it is possible to detect the detection target substance with sensitivity on a molecule-by-molecule basis (e.g., see the invention described in Patent Document 1).

As a substrate used in such a "unimolecular enzyme assay" method, examples are various polymer resins such as polydimethyl siloxane or soft materials such as silicone rubber, and the substrate is obtained by thermoset molding (e.g., see the invention described in Patent Document 2).

Further, there are proposed bioassay plates formed by thermo-press molding or injection molding thermoplastic resins such as polystyrene and cycloolefin polymer (see the invention described in Patent Document 3). Furthermore, resins that do not emit autofluorescence are proposed as resins applied to the bioassay plate (see the invention described in Patent Document 4).

Moreover, for the purpose of uniforming temperature control of the entire chip surface in enzyme processing and PCR reaction, microwell chips with minute capacity are proposed where through holes formed by microinjection molding are enclosed with thin films (see the invention described in Patent Document 5).

PRIOR ART DOCUMENT

Patent Document

[Patent Document 1] Japanese Unexamined Patent Publication No. 2011-137830
[Patent Document 2] Japanese Unexamined Patent Publication No. 2004-309405
[Patent Document 3] Japanese Unexamined Patent Publication No. 2018-529968
[Patent Document 4] Japanese Unexamined Patent Publication No. 2005-134339
[Patent Document 5] Japanese Unexamined Patent Publication No. 2003-70456
[Patent Document 6] Japanese Unexamined Patent Publication No. 2008-44283

DISCLOSURE OF INVENTION

Problems to be Solved by the Invention

However, in the substrate described in Patent Document 2, since thermoset molding is used, a long time is required to obtain the substrate, and productivity is poor. Further, due to low productivity, disadvantage is made in the respect of manufacturing costs.

Further, in the bioassay plate described in Patent Document 3, there are the following problems. In other words, since an injection molding apparatus and a mold used in injection molding are expensive, the bioassay plate manufactured by injection molding is at a disadvantage from the viewpoint of manufacturing costs. Therefore, in the bioassay plate described in Patent Document 3, it is difficult to support small lot-manufacturing from the viewpoint of costs.

Furthermore, the bioassay plate described in Patent Document 3 is a plate-shaped form with a thickness to some extent. This is because molding of a thin molded product by injection molding tends to generate a problem of short shots where the mold is not completely filled with the resin. The short shot is capable of being resolved by increasing an injection pressure, however, in this case, fins are apt to occur in the molded product, and are made a factor of failure. Therefore, the plate requires a thickness more than some extent.

Moreover, to thin the bioassay plate, a resin fill path is narrow in injection molding, a problem thereby occurs to degrade productivity, and it is difficult to make thinning up to some extent.

From the foregoing, in molding by injection molding, in terms of industrial manufacturing, it is conceived that the thickness capable of being implemented is provided with a lower limit of 300 μm to 400 μm. Since there is the lower limit in the thickness of the bioassay plate, there is a problem that the lower limit is a barrier in miniaturizing an analytical apparatus using the bioassay plate.

Further, similarly, also in the thermo-press molding described in Patent Document 3, flowability is required in resin with high viscosity, and therefore, by the same reason as described above, thinning is difficult.

Then, both of injection molding and thermo-press needs a coiling process after forming, requires a long time for manufacturing, is at a disadvantage from the viewpoints of manufacturing costs and production quantity, and has high usage limitation in terms of industry.

Further, the "unimolecular enzyme assay" method is an enzyme reaction, and therefore, tends to undergo an effect of a temperature environment. Particularly, there is an issue of the so-called edge effect where wells existing in the outer region of the substrate undergo an effect of a peripheral temperature and the reaction thereby proceeds higher (or slower) than the other wells.

In order to resolve the problem in thinning by injection molding, in the invention described in Patent Document 5, a plate having through holes is formed by injection molding, and then, is enclosed with a thin film to obtain a microwell plate.

However, since the microwell plate described in Patent Document 5 also requires injection molding, it is necessary to thicken a plate having through holes, it is not possible to further narrow distances between respective concave portions, and it is not possible to increase the concave-portion density inside the plane required for the "unimolecular enzyme bioassay" method.

Moreover, since fluorescence is used in marker detection of the nucleic acid, protein, virus, cell and so on, the substrate for bioassay is required to have low autofluorescence properties with low fluorescence emitted from the substrate for bioassay itself. However, in the case of applying the above-mentioned technique, there is the lower limit in thickness of the molded product as described previously, and therefore, even in using materials with low autofluorescence properties, there is an issue that it is not possible to control autofluorescence properties within up to some extent. This is because the low autofluorescence property of a substrate is determined by the product of the autofluorescence property specific to the material and the thickness.

On the other hand, as one of fine processing methods except injection molding, there is a optical imprint technique using photosensitive resin compositions (e.g., see the invention described in Patent Document 6.). However, as described previously, the low autofluorescence property is required for the substrate for bioassay, and there has been not a proposed bioassay substrate comprised of photosensitive resin having the low autofluorescence property.

Further, in the above-mentioned optical imprint technique, a substrate film capable of forming a fine shape is indispensable, and as the substrate film made of resin with low autofluorescence, there are polystyrene, cycloolefin polymer and the like. Particularly, cycloolefin polymer substrate films are excellent in transparency and low autofluorescence properties and are suitable as substrates for bioassay, but are low in adhesion to the photosensitive resin applied to the optical imprint technique. Therefore, it has been difficult to form a substrate for bioassay comprised of cycloolefin polymer as a substrate film and the photosensitive resin having the low autofluorescence property.

The present invention was made in view of the above-mentioned issue, it is an object of the invention to provide microwell films for bioassay which are high in applicability in industry at low cost, capable of developing the low autofluorescence property, easy to perform temperature control of wells, and capable of suppressing the edge effect in substrates for bioassay applied to the "unimolecular enzyme assay" method and the like, methods of manufacturing the films, and further, photosensitive resin compositions for formation of the microwell films for bioassay.

Means for Solving the Problem

A microwell film for bioassay of the present invention is characterized by being comprised of at least a substrate, and a resin layer having microwells on its surface provided on one main surface of the substrate, where in the substrate and the resin layer, an absorption coefficient at each of wavelengths of 350 nm to 800 nm is 0.01 $\mu m^{-1}$ or less.

Further, in the microwell film for bioassay of the present invention, it is preferable that the absorption coefficient of the resin layer at a wavelength of 300 nm is 0.02 $\mu m^{-1}$ or less, and is a maximum value among respective absorption coefficients at wavelengths of 300 nm to 800 nm.

Furthermore, in the microwell film for bioassay of the present invention, it is preferable that the resin layer is a cured material of a photosensitive resin composition derived from at least a photopolymerizable monomer and at least a photopolymerizable oligomer.

Particularly, it is further preferable that the resin layer is a cured material of a photosensitive resin composition containing at least a nitrogen-containing photopolymerizable monomer.

By such a configuration, it is possible to obtain a microwell film for bioassay having microwells suitable for the "unimolecular enzyme assay" method by the optical imprint method using the photopolymerizable monomer with the low autofluorescence property and low viscosity.

Further, in the microwell film for bioassay of the present invention, it is preferable that the substrate is polyethylene terephthalate, polycarbonate, cycloolefin polymer, polydimethylsiloxane or polystyrene.

Furthermore, in the microwell film for bioassay of the present invention, it is preferable that the substrate and the resin layer contain nitrogen elements, an average nitrogen element concentration (Nf) of the resin layer is higher than an average nitrogen element concentration (Ns) of the substrate, and that the substrate has a region with a nitrogen element concentration (Ni) meeting the following equation (1) on the first main surface side provided with the resin layer.

$$Nf > Ni > Ns \quad \text{Equation (1)}$$

Still furthermore, in the microwell film for bioassay of the present invention, in the resin layer, it is preferable that a ratio between a fluorine element concentration (Fs) of the surface of the resin layer and an average fluorine element concentration (Fb) in the resin layer meets the following equation (2).

$$1 < Fs/Fb \leq 1500 \quad \text{Equation (2)}$$

A photosensitive resin composition for formation of the microwell film for bioassay of the present invention is characterized by being a photosensitive resin composition for formation of the microwell film for bioassay containing (A) photopolymerizable monomer, (B) photopolymerizable oligomer, and (C) photopolymerization initiator, where a content of the (A) photopolymerizable monomer is 10 to 80 percent by weight relative to weight of the photosensitive resin composition, a content of the (B) photopolymerizable oligomer is 10 to 80 percent by weight relative to the weight of the photosensitive resin composition, a content of the (C) photopolymerization initiator is 0.5 to 10 percent by weight relative to the weight of the photosensitive resin composition, and the absorption coefficient at each of wavelengths of 350 nm to 800 nm after curing is 0.01 $\mu m^{-1}$ or less.

Further, in the photosensitive resin composition for formation of the microwell film for bioassay of the present invention, it is preferable that the (C) photopolymerization initiator is an α-hydroxyalkyl phenon-based polymerization initiator.

Furthermore, in the photosensitive resin composition for formation of the microwell film for bioassay of the present invention, it is preferable that the (A) photopolymerizable monomer contains a fluorine-containing (meth)acrylate expressed by the following chemical formula (1).

[Chemistry 1]

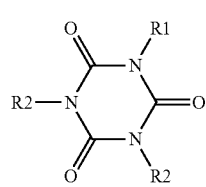

Chemical formula (1)

(In the chemical formula (1), R1 represents the following chemical formula (2), and R2 represents the following chemical formula (3).)

[Chemistry 2]

Chemical formula (2)

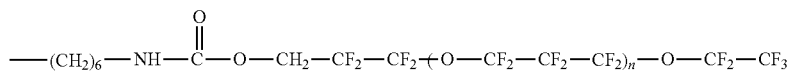

(In the chemical formula (2), n is an integer ranging from "1" to "6".)

[Chemistry 3]

Chemical formula (3)

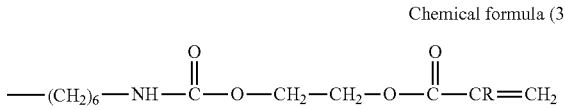

(In the chemical formula (3), R represents H or $CH_3$.)

Still furthermore, in the photosensitive resin composition for formation of the microwell film for bioassay of the present invention, it is preferable that the (A) photopolymerizable monomer contains a nitrogen-containing photopolymerizable monomer.

Further, a method of manufacturing the microwell film for bioassay of the present invention is characterized by including a step of applying the photosensitive resin composition for formation of the microwell film for bioassay onto a predetermined substrate or a master mold, a step of pressing the photosensitive resin composition between the substrate and the master mold, a step of curing the photosensitive resin composition by exposure to light to obtain a cured material, and a step of peeling off the cured material from the master mold.

Furthermore, a method of manufacturing the microwell film for bioassay of the present invention is characterized by including a step of applying the photosensitive resin composition for formation of the microwell film for bioassay where the (A) photopolymerizable monomer contains a nitrogen-containing photopolymerizable monomer onto at least a predetermined substrate, a penetration step of the photosensitive resin composition in the substrate, a step of pressing between the substrate and the master mold, a step of curing the photosensitive resin composition by exposure to light to obtain a cured material, and a step of peeling off the cured material from the master mold.

For example, the microwell film for bioassay of the present invention is applied to the unimolecular enzyme assay method.

Advantageous Effect of the Invention

According to the present invention, it is possible to provide the microwell film for bioassay that is a bioassay substrate which has the autofluorescence property lower than in the bioassay plate by conventional injection molding, is capable of being manufactured at low cost, is easy to perform temperature control of wells, is capable of suppressing the edge effect, and is applied to the "unimolecular enzyme assay" method and the like. Further, it is possible to provide the photosensitive resin composition capable of forming the microwell film for bioassay which is low in autofluorescence property and is easy to detect a marker, and the method of manufacturing the microwell film for bioassay using the photosensitive resin composition.

BEST MODE FOR CARRYING OUT THE INVENTION

One Embodiment (hereinafter, simply described as "this Embodiment") of the present invention will be described below in detail. In addition, the present invention is not limited to the following Embodiment, and is capable of being carried into practice with various modifications within a scope of the subject matter of the invention. Notation of "~" indicative of a numerical range is meaning including a lower limit value and an upper limit value.

Microwell films for bioassay and methods of manufacturing the film according to this Embodiment will be described below in detail. In addition, (meth)acrylate means acrylate or methacrylate.

<<Microwell Film for Bioassay>>

A microwell film for bioassay of this Embodiment is a microwell film having microwells that is a fine concave structure on its surface, and is comprised of at least a substrate, and a resin layer provided on a first main surface of the substrate to have microwells on its surface.

Further, in this Embodiment, resins forming the substrate and resin layer are characterized by that an absorption coefficient at each of wavelengths of 350 nm to 800 nm is 0.01 $\mu m^{-1}$ or less.

Since the film is comprised of the substrate and the resin layer having microwells, it is possible to thin the thickness of the entire well film and uniform the thickness inside the surface. By having the substrate, since it is possible to ensure thickness uniformity of the entire film, the resin layer having microwells is enough to be a thickness required only to form the microwell, and as a result, it is possible to suppress variations in thickness of the entire well film.

As described previously, the "unimolecular enzyme assay" method is an enzyme reaction, and therefore, tends to undergo an effect of a temperature environment. Particularly, the issue is the so-called edge effect where wells existing in the outer region of the substrate undergo an effect of a peripheral temperature and the reaction thereby proceeds higher (or slower) than the other wells. In order to resolve the issue, by thinning the well film, temperature control is easy by a temperature-control plate on the backside of the well film, and the edge effect in the substrate outer region is relatively suppressed. Further, by suppressing variations in thickness of the entire well film, variations in temperature control are further suppressed.

Particularly, since it is easy to make a thin film thinner than the lower limit thickness of a molded plate by conventional injection molding, the above-mentioned effect is obtained that temperature control of the well film is easy, and that in-plane uniformity is excellent.

Figure 1:
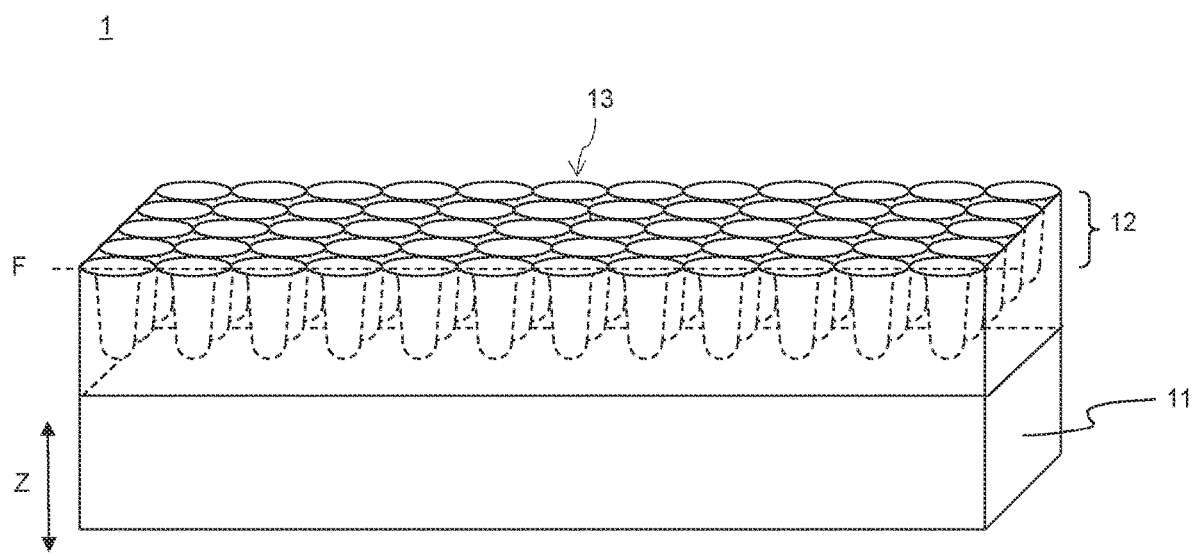
FIG. 1 a schematical perspective view showing an example of a microwell film for bioassay of this Embodiment.

FIG. 1 illustrates a perspective cross-sectional schematic view of a microwell film for bioassay as one Embodiment of the present invention.

In the example shown in FIG. 1, a microwell film for bioassay 1 is in the form of a film, and is provided with a substrate 11, and a resin layer 12 having microwells provided on a first main surface of the substrate 11. The resin layer 12 contains a plurality of concave portions 13 provided to extend from the main surface (first main surface) F of the microwell film for bioassay 1 toward the in-plane direction (toward a second main surface (backside) on the opposite side to the first main surface). The plurality of concave portions 13 is provided to be dented toward below (inside the microwell film for bioassay 1) from the main surface F in a thickness direction (Z-axis direction) perpendicular to the main surface F of the microwell film for bioassay 1. Each of the plurality of concave portions 13 is arranged at a predetermined pitch.

The microwells in this Embodiment are not limited particularly, as long as the microwells are a fine concave structure suitable for bioassay that is usage thereof. Preferably, the concave portion is a hole structure.

The cross-sectional shape of the concave portion with the hole structure may be a rectangle, square, trapezoid, shape having a curvature in a corner portion thereof or the like, and a circle. Further, a top plane shape of the concave portion with the hole structure may be a rectangle, square, trapezoid, rhombus, hexagon, triangle, shape having a curvature in a corner portion thereof or the like, and a circle.

Further, these pattern arrangements of the concave portions with the hole structure are selected corresponding to a use as appropriate, and are not particularly limited.

For example, the arrangement may be a pattern shape where the concave portions with the hole structure are arranged randomly and are formed substantially uniformly inside the plane, or a periodically arranged pattern shape. Particularly, when the arrangement is a pattern shape where the concave portions with the hole structure are arranged periodically to form an array, such an arrangement is made easy to detect a target substance in the "unimolecular enzyme assay" method, and is thereby preferable.

Figure 2:
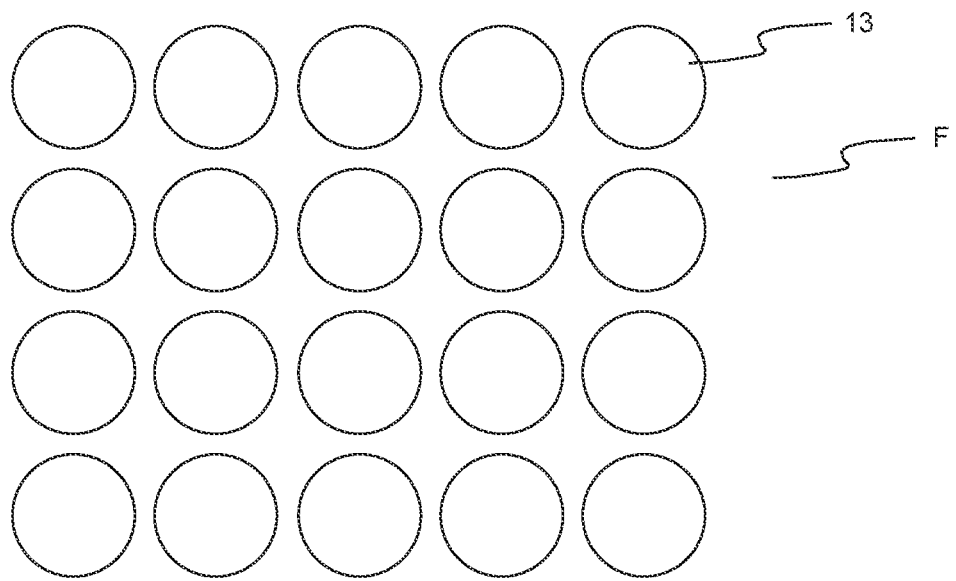
FIG. 2 is a plan schematic view showing one example of a pattern of microwells in the microwell film for bioassay of this Embodiment.

FIG. 2 is a plan schematic view of the microwell film for bioassay 1 according to this Embodiment. As shown in FIG. 2, the concave portions 13 with the hole structure formed in the main surface F of the resin layer 12 including the microwells are arranged at certain intervals at mutually same pitches, and form a tetragonal arrangement.

Figure 3:
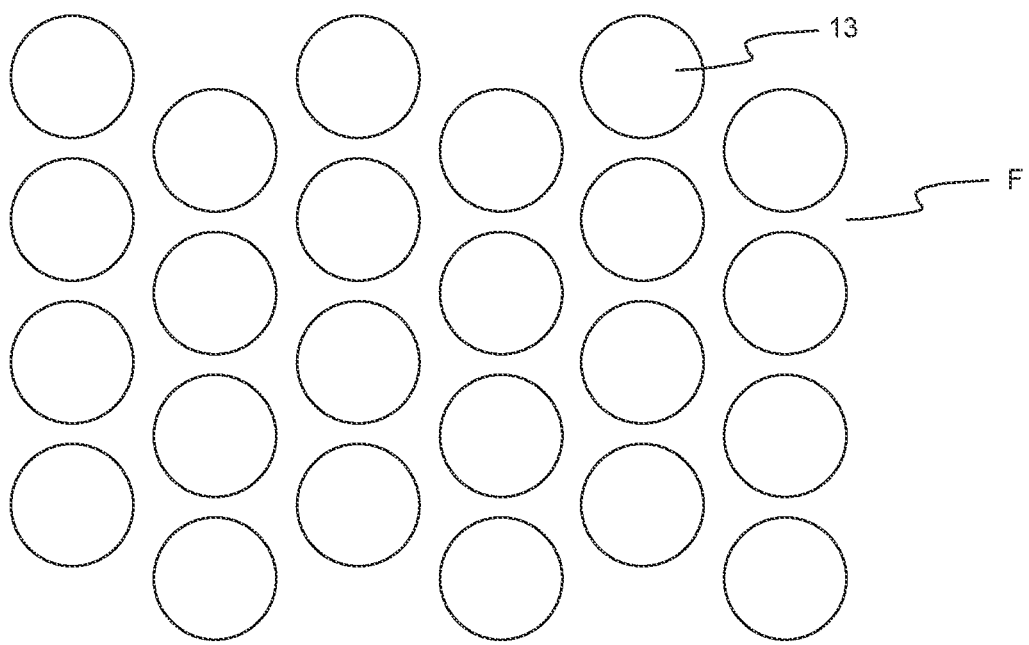
FIG. 3 is a plan schematic view showing another example of the pattern of microwells in the microwell film for bioassay of this Embodiment.

FIG. 3 is a plan schematic view showing another example of the microwell film for bioassay 1 according to this Embodiment. As shown in FIG. 3, the concave portions 13 with the hole structure formed in the main surface F of the resin layer 12 including the microwells are arranged at certain intervals at mutually same pitches, and form a trigonal arrangement.

As a size of the concave portion 13 with the hole structure in this Embodiment, sizes suitable for bioassay that is a use thereof are selected, and the size is not particularly limited.

For example, in the case where the top plane shape of the hole structure is a circle, a diameter thereof is preferably in a range from 50 nm to 100 μm. The diameter in a range from 100 nm to 50 μm adapts to bioassays in the region from RNA to cell detection, and is preferable. Further, the diameter in a range from 200 nm to 10 μm is the most suitable for "unimolecular enzyme assay", and is particularly preferable.

Further, a depth of the hole structure is preferably in a range from 50 nm to 100 μm, the diameter in a range from 100 nm to 50 μm adapts to bioassay by the same reason as described above and is preferable, and further, a range from 200 nm to 10 μm is the most suitable for "unimolecular enzyme assay" as described above, and is particularly preferable.

The pitch between respective concave portions 13 in this Embodiment preferably ranges from 200 nm to 400 μm, with a pitch in the range of 400 nm to 200 μm being preferable because detection of a target substance in bioassay is made easy, and particularly preferably ranges from 800 nm to 40 μm because detection sensitivity in "unimolecular enzyme assay" is maximum.

Herein, the pitch between respective concave portions in this Embodiment is a shortest distance between centers of each hole and another holes that are most recently in contact with it, and in the pattern shape where the portions are periodically arranged, is a periodic pitch. In the case where the concave portions with the hole structure are randomly disposed, the pitch is an average value of most adjacent distances of the portions.

In the microwell film for bioassay of this Embodiment, in the substrate 11 and resin layer 12 including microwells, the absorption coefficient at each of wavelengths of 350 nm to 800 nm is 0.01 $\mu m^{-1}$ or less.

(Absorption Coefficient)

By controlling the absorption coefficient within 0.01 $\mu m^{-1}$ or less, it is possible to obtain the microwell film for lowering the autofluorescence property in wavelengths of 350 nm to 800 nm. Fluorescence emission is a mechanism for absorbing excitation light with a particular wavelength, and by energy thereof, emitting fluorescence with a wavelength longer than the excitation light. Therefore, by suppressing the absorption coefficient, there is a tendency capable of suppressing also fluorescence properties.

On the other hand, as described previously, in the microwell film of this Embodiment, since the thickness of the resin layer having microwells is thin, it is possible to suppress variations in temperature control of the film. Therefore, the resin layer having microwells is preferably a cured material of a photosensitive resin composition containing photopolymerizable monomers. In addition, the resin layer is preferably a cured material of a photosensitive resin composition derived from the photopolymerizable monomer and photopolymerizable oligomer. However, the photopolymerizable monomer is cured by light irradiation, thereby requires a high absorption coefficient at a wavelength for light curing, and is contradictory to suppression of the autofluorescence property described previously.

As a result of keen studies, the inventors of the present invention found out that a cured material of a photosensitive resin composition containing a photopolymerizable monomer is also capable of suppressing the autofluorescence property, when the absorption coefficient at each of wavelengths of 350 nm to 800 nm is 0.01 $\mu m^{-1}$ or less in a resin layer having microwells. By setting the absorption coefficient of the cured material after photopolymerization at the value described above, it is possible to suppress the autofluorescence property, while maintaining reactivity of the photopolymerizable monomer.

Details are uncertain about the fact that the cured material of the photosensitive resin composition containing the photopolymerizable monomer is also capable of suppressing the autofluorescence property, when the absorption coefficient at each of wavelengths of 350 nm to 800 nm is 0.01 $\mu m^{-1}$ or less, but is estimated as described below.

First, from the study of the inventors of the present invention, it is made clear that the autofluorescence property of the microwell film is proportional to the absorption coefficient at each of wavelengths of 350 nm to 800 nm. For fluorescence emission, it is necessary to absorb light with a wavelength shorter than the fluorescence wavelength, and it is estimated that the absorbed light with the wavelength becomes fluorescence by particular fluorescence conversion efficiency.

The microwell film of this Embodiment is comprised of the substrate 11 and the resin layer 12 including microwells. A general flat film is used as the substrate 11, is thinner than a molded product by injection molding of conventional techniques, and is approximately in a range of 50 μm to 188 μm.

Further, the thickness of the resin layer 12 including microwells described previously is a sum of an average thickness except a concave-portion volume of the hole structure and a thickness of a thinnest portion of the concave-portion bottom, and approximately ranges from 10 μm to 15 μm.

From the foregoing, in the case of using a resin having the same autofluorescence property as that of the resin used in conventional injection molding for the substrate 11 of the microwell film, when the following equation (3) holds, at least, the resultant has the autofluorescence property equal to or less than the thinnest molded product by injection molding of conventional techniques.

Autofluorescence Property of the Substrate 11+Autofluorescence Property of the Resin Layer 12

<autofluorescence property by injection molding thinnest thickness>  Equation (3)

Autofluorescence property∝absorption coefficient× thickness  Equation (4)

Equation (5) is obtained from Equation (3) and Equation (4).

Absorption coefficient$A$ of the resin layer 12<(thinnest molded product by injection molding−the substrate 11)×absorption coefficient$B$  Equation (5)

Herein, the absorption coefficients A and B are respectively absorption coefficients of the resin layer 12 and substrate 11 or thinnest molded product.

At the time of the resin layer 12 with the absorption coefficient A meeting the Equation (5), it is possible to obtain the microwell film for bioassay having the autofluorescence property lower than that of the bioassay plate by conventional injection molding.

Further, as a result of keen studies of the inventors, when the absorption coefficient of the resin layer 12 at each of wavelengths of 350 nm to 800 nm is 0.01 $\mu m^{-1}$ or less, it is possible to obtain microwell films for bioassay having low autofluorescence properties.

Furthermore, when the absorption coefficient of the resin layer 12 at each of wavelengths of 350 nm to 800 nm is 0.005 $\mu m^{-1}$ or less, due to lower autofluorescence properties, biomarker detection by fluorescence is made easy and such a resin layer 12 is preferable. When such an absorption coefficient is 0.001 $\mu m^{-1}$ or less, also in "unimolecular enzyme assay" with minute well volume and low fluorescence intensity of a biomarker, by suppressing a background signal by the substrate, it is possible to decrease detection sensitivity, and such a resin layer is particularly preferable.

Still furthermore, in the microwell film for bioassay of this Embodiment, it is preferable that the absorption coefficient of the resin layer 12 at a wavelength of 300 nm is 0.02 $\mu m^{-1}$ or less, and is a maximum value among respective absorption coefficients at wavelengths of 300 nm to 800 nm.

In the distribution of the above-mentioned absorption coefficients, since a wavelength indicative of a peak of the absorption coefficient is 300 nm or less, in the case of adopting the cured material of the photosensitive resin composition containing the photopolymerizable monomer into the resin layer 12 in the microwell film for bioassay of this Embodiment, it is possible to obtain good photocuring properties and the microwell film for bioassay having the low autofluorescence property, and such a case is preferable.

In the resin layer 12, in addition to the fact that the absorption coefficient at each of wavelengths of 350 nm to 800 nm is 0.01 $\mu m^{-1}$ or less, when the wavelength indicative of the peak of the absorption coefficient is 300 nm or less, it is possible to obtain the microwell film for bioassay having the low autofluorescence property. This reason is estimated as described below.

As described previously, fluorescence emission is the mechanism for absorbing excitation light with a particular wavelength, and by energy thereof, emitting fluorescence with a wavelength longer than the excitation light. Since absorption of polymer forming the microwell film for bioassay shows broad absorption with a particular wavelength being the center, in the case of having an absorption peak at a wavelength region exceeding 300 nm, it is made difficult to obtain good low autofluorescence properties, and such a case is not preferable.

In the microwell film for bioassay of this Embodiment, when the absorption coefficient of the resin layer 12 at the wavelength of 300 nm is a maximum value among respective absorption coefficients at wavelengths of 300 nm to 800 nm, and is 0.01 $\mu m^{-1}$ or less, due to lower autofluorescence properties, biomarker detection by fluorescence is made easy and such a resin layer 12 is preferable. When the absorption coefficient is 0.002 $\mu m^{-1}$ or less, also in "unimolecular enzyme assay" with minute well volume and low fluorescence intensity of a biomarker, by suppressing a background signal by the substrate, it is possible to decrease detection sensitivity, and such a resin layer is particularly preferable.

Further, in the substrate 11 in the microwell film for bioassay of this Embodiment, when the absorption coefficient at each of wavelengths of 350 nm to 800 nm is 0.01 $\mu m^{-1}$ or less, it is possible to suppress the autofluorescence property, while maintaining reactivity of the photopolymerizable monomer.

In addition, the "absorption coefficient" in the present Description is obtained from the following Equation (6).

Absorption coefficient=Absorbance/film thickness (μm)  Equation (6)

Further, the absorbance is calculated according to the following Equation (7).

Absorbance=−log(light transmittance)  Equation (7)

The light transmittance is obtained by measuring with a general spectrophotometer, and for example, there is Spectrophotometer UV-2500 (made by Shimadzu Corporation).

<Substrate>

For edge effect suppression of the microwell film for bioassay of this Embodiment as described above, a thickness of the substrate in this Embodiment is preferably in a range of 10 μm to 300 μm, more preferably 20 μm or more in terms of handling of the microwell film, and more preferably 200 μm or less because temperature control of the microwell film is easy to perform.

Further, for the similar reason, with respect to a thickness of the resin layer having microwells of this Embodiment, a thickness of a thinnest portion of a well bottom is preferably in a range of 1 nm to 10 μm, and more preferably in a range of 10 nm to 1 μm because it is possible to more suppress variations in temperature control of the microwell film.

As materials of the substrate, as long as the absorption coefficient at each of wavelengths of 350 nm to 800 nm is 0.01 $\mu m^{-1}$ or less, the materials are not limited particularly, and it is possible to use inorganic materials such as glass and ceramic and organic materials such as plastic. The form of a film having foldability and excellent in successive productivity is preferable, and it is possible to use composite materials with a thin film, fabric, nonwoven fabric and the like. Preferable examples are polyethylene terephthalate, polycarbonate, cycloolefin polymer, polydimethylsiloxane and polystyrene.

Particularly, the cycloolefin polymer is excellent in transparence over ultraviolet to infrared regions, has low autofluorescence properties in this wavelength region, and therefore, is particularly preferable. There are ZEONOR Film (Registered Trademark) made by ZEON CORPORATION, and ARTON (Registered Trademark) film made by JSR Corporation made of such cycloolefin polymers.

A thickness of the substrate in the microwell film for bioassay of this Embodiment is not limited particularly, as long as it is possible to form the resin layer having microwells on its surface, however, from above Equation (5), at least, if it is thinner than the thinnest molded product by general injection molding, it is possible to obtain the effects of the present invention such that well temperature control is easy to enable the edge effect to be suppressed, and that it is further possible to suppress autofluorescence properties to make biomarker detection easy.

For the above-mentioned reason, the thickness of the substrate is preferably 300 μm or less, preferably 200 μm or less because the entire microwell film thickness including the surface resin layer is thinner than the thinnest molded product by injection molding to enable the edge effect to be suppressed, and more preferably 190 μm or less to enable the autofluorescence property to be suppressed.

<Resin Layer>

As photopolymerizable monomers forming the cured product constituting the resin layer having microwells in the microwell film for bioassay of this Embodiment, as long as the absorption coefficient at each of wavelengths of 350 nm to 800 nm is 0.01 $\mu m^{-1}$ or less in the resin layer containing the monomer and the monomer is photopolymerizable, the monomer is not particularly limited, includes radical polymerization-based monomers and cation polymerization-based monomers, and may contain a fluororesin. In the case of containing the fluororesin, since surface liquid repellency is developed, formation of a minute droplet is promoted in the microwell in bioassay, and such a case is preferable.

As photopolymerizable radical polymerization-based resins forming the resin layer having microwells, for example, it is possible to use a resin composition that is a mixture of (meth)acrylate which is a photopolymerizable monomer, photopolymerizable oligomer and photopolymerization initiator.

The (meth)acrylate is not particularly limited as long as the glass transition temperature after curing is 100° C. or more, and more preferably, 120° C. or more. Preferable are monomers having acryloyl groups or methacryloyl groups, monomers having vinyl groups and monomers having allyl groups, and the monomers having acryloyl groups or methacryloyl groups are more preferable. Herein, the glass transition temperature after curing means a glass transition temperature with respect to a cured material of a mixture of used (meth)acrylates. In other words, for example, in using (meth)acrylate A, (meth)acrylate B and (meth)acrylate C, also in the case where glass transition temperatures of cured (meth)acrylates A, B and C are respectively 60° C., 100° C. and 120° C., when the glass transition temperature is 105° C. after curing a mixture thereof ((meth)acrylate A+(meth)acrylate B+(meth)acrylate C), it is assumed that 105° C. is adopted as the glass transition temperature.

Preferable as the photopolymerizable monomer are polyfunctional monomers provided with a plurality of polymerizable groups, and the number of polymerizable groups is preferably an integer of from "1" to "6" in terms of excellent polymerizable properties. Further, in the case of mixing two or more kinds of polymerizable monomers to use, the average number of polymerizable groups preferably ranges from "2" to "5". In the case of using a single monomer, in order to increase crosslinking points after polymerization reaction and obtain physical stability (strength, heat resistance, etc.) of the cured material, a monomer with the number of polymerizable groups being "3" or more is preferable. Further, in the case of a monomer with the number of polymerizable groups being "1" or "2", it is preferable to use together with a monomer with the different number of polymerizable groups.

Specific examples of (meth)acrylate monomers include the following compounds. Examples of monomers having an acryloyl group or a methacryloyl group are (meth)acrylic acids, aromatic (meth)acrylates [phenoxyethyl acrylate, benzyl acrylate, etc.], hydrocarbon-based (meth)acrylates [stearyl acrylate, lauryl acrylate, 2-ethylhexyl acrylate, allyl acrylate, 1,3-butanediol diacrylate, 1,4-butanediol diacrylate, 1,6-hexanediol diacrylate, trimethylolpropane triacrylate, pentaerythritol triacrylate, dipentaerythritol hexaacrylate, etc.], ethereal oxygen atom-containing hydrocarbon-based (meth)acrylates [ethoxyethyl acrylate, methoxyethyl acrylate, glycidyl acrylate, tetrahydrofurfuryl acrylate, diethylene glycol diacrylate, neopentylglycol diacrylate, polyoxyethylene glycol diacrylate, tripropylene glycol diacrylate, etc.], functional group-containing hydrocarbon-based (meth)acrylates [2-hydroxyethyl acrylate, 2-hydroxypropyl acrylate, 4-hydroxybutyl vinyl ether, N,N-diethylamino ethyl acrylate, N,N-dimethylamino ethyl acrylate, (dimethylamino)ethyl methacrylate, etc.], and silicone-based acrylates. Other samples are EO-modified glycerol tri(meth)acrylate, ECH-modified glycerol tri(meth)acrylate, PO-modified glycerol tri(meth)acrylate, pentaerythritol triacrylate, EO-modified phosphoric acid triacrylate, trimethylolpropane tri(meth)acrylate, caprolactone-modified trimethylolpropane tri(meth)acrylate, PO-modified trimethylolpropane tri(meth)acrylate, tris(acryloxyethyl) isocyanurate, EO-modified trimethylolpropane tri(meth)acrylate, dipentaerythritol hexa(meth)acrylate, caprolactone-modified dipentaerythritol hexa(meth) acrylate, dipentaerythritol hydroxy penta(meth)acrylate, alkyl-modified dipentaerythritol penta(meth)acrylate, dipentaerythritol poly(meth)acrylate, ditrimethylol propane tetra (meth)acrylate, alkyl-modified dipentaerythritol tri(meth) acrylate, pentaerythritol ethoxy tetra(meth)acrylate, pentaerythritol tetra(meth)acrylate, diethylene glycol monoethyl ether (meth)acrylate, dimethylol dicyclopentane di(meth)acrylate, di(meth)acrylated isocyanurate, 1,3-butylene glycol di(meth)acrylate, 1,4-butanediol di(meth)acrylate, EO-modified 1,6-hexanediol di(meth)acrylate, ECH-modified 1,6-hexanediol di(meth)acrylate, acryloxy polyethylene glycol acrylate, 1,9-nonanediol di(meth)acrylate, EO-modified bisphenol A di(meth)acrylate, PO-modified bisphenol A di(meth)acrylate, modified-bisphenol A di(meth)acrylate, EO-modified bisphenol F di(meth)acrylate, ECH-modified hexahydrophthalic acid diacrylate, neopentyl glycol di(meth)acrylate, hydroxy pivalic acid neopentyl glycol di(meth)acrylate, EO-modified neopentyl glycol diacrylate, PO-modified neopentyl glycol diacrylate, caprolactone-modified hydroxy pivalic acid ester neopentyl glycol, stearic acid-modified pentaerythritol di(meth)acrylate, ECH-modified propylene glycol di(meth)acrylate, ECH-modified phthalic acid di(meth)acrylate, poly(ethylene glycol-tetramethylene glycol) di(meth)acrylate, poly(propylene glycol-tetramethylene glycol) di(meth)acrylate, polypropylene glycol di(meth)acrylate, silicone di(meth) acrylate, tetraethylene glycol di(meth)acrylate, triethylene glycol di(meth)acrylate, polyester (di)acrylate, polyethylene glycol di(meth)acrylate, dimethylol tricyclodecane di(meth) acrylate, neopentyl glycol-modified trimethylol propane di(meth)acrylate, dipropylene glycol di(meth)acrylate, tripropylene glycol di(meth)acrylate, triglycerol di(meth) acrylate, EO-modified tripropylene glycol di(meth)acrylate, divinyl ethylene urea, divinyl propylene urea, 2-ethyl-2-butyl propanediol acrylate, 2-ethylhexyl (meth)acrylate, 2-ethylhexyl carbitol (meth)acrylate, 2-hydroxyethyl (meth) acrylate, 2-hydroxypropyl (meth)acrylate, 2-hydroxybutyl (meth)acrylate, 2-methoxyethyl (meth)acrylate, 3-methoxybutyl (meth)acrylate, 4-hydroxybutyl (meth)acrylate, acrylic acid dimer, benzyl (meth)acrylate, butanediol mono(meth) acrylate, butoxyethyl (meth)acrylate, butyl (meth)acrylate, cetyl (meth)acrylate, EO-modified cresol (meth)acrylate, ethoxyed phenyl (meth)acrylate, ethyl (meth)acrylate, dipropylene glycol (meth)acrylate, isoamyl (meth)acrylate, isobutyl (meth)acrylate, iso-octyl (meth)acrylate, cyclohexyl (meth)acrylate, dicyclo pentanyl (meth)acrylate, isobornyl (meth)acrylate, dicyclo pentanyl oxyethyl (meth) acrylate, iso myristyl (meth)acrylate, lauryl (meth)acrylate, methoxy dipropylene glycol (meth)acrylate, methoxy polyethylene glycol (meth)acrylate, methoxy triethylene glycol (meth)acrylate, methyl (meth)acrylate, methoxy tripropylene glycol (meth)acrylate, neopentyl glycol benzoate (meth) acrylate, nonylphenoxy polyethylene glycol (meth)acrylate; nonylphenoxy polypropylene glycol (meth)acrylate, octyl (meth)acrylate, paracumyl phenoxy ethylene glycol (meth) acrylate, ECH-modified phenoxy acrylate, phenoxy diethylene glycol (meth)acrylate; phenoxy hexaethylene glycol (meth)acrylate, phenoxy tetraethylene glycol (meth)acrylate, phenoxy ethyl (meth)acrylate, polyethylene glycol (meth)acrylate, polyethylene glycol-polypropylene glycol (meth)acrylate, polypropylene glycol (meth)acrylate, stearyl (meth)acrylate; EO-modified succinic acid (meth)acrylate; tert-butyl (meth)acrylate, tribromo phenyl (meth)acrylate, EO-modified tribromo phenyl (meth)acrylate, tridodecyl (meth)acrylate, isocyanuric acid EO-modified di and triacrylate, ε-caprolactone-modified tris(acryloxyethyl) isocyanurate, ditrimethylol propane tetraacrylate and the like. Examples of monomers having an ally group include ρ-isopropenyl phenol. Examples of monomers having a vinyl group include styrene, α-methyl styrene, acrylonitrile, and vinylcarbazole. In addition, EO-modified means ethylene oxide-modified, ECH-modified means epichlorohydrin-modified, and PO-modified means propylene oxide-modified. Further, as bisphenol Abased compounds, it is also possible to adopt dimethacrylate of polyalkylene glycol where to opposite ends of bisphenol A are added average two moles of propylene oxides and average six moles of ethylene oxides respectively, dimethacrylate (NK ESTER BPE-500 made by Shin-Nakamura Chemical Co., Ltd.) of polyethylene glycol where to each of opposite ends of bisphenol A are added average five moles of ethylene oxides, and dimethacrylate (NK ESTER BPE-200 by made by Shin-Nakamura Chemical Co., Ltd.) of polyethylene glycol where to each of opposite ends of bisphenol A are added average two moles of ethylene oxides. Examples thereof are 1,6-hexanediol (meth)acrylate, 1,4-cyclohexanedioldi(meth)acrylate, polypropylene glycol di(meth)acrylate, polyethylene glycol di(meth)acrylate, 2-di(p-hydroxyphenyl) propane di(meth) acrylate, glycerol tri(meth)acrylate, trimethylolpropane tri (meth)acrylate, polyoxypropyl trimethylolpropane tri(meth) acrylate, polyoxyethyl trimethylolpropane triacrylate, pentaerythritol tetra(meth)acrylate, dipentaerythritol penta (meth)acrylate, trimethylolpropane triglycidyl ether (meth) acrylate, bisphenol A diglycidyl ether di(meth)acrylate, β-hydroxypropyl-β'-(acryloyloxy)propyl phthalate, phenoxy polyethylene glycol (meth)acrylate, nonylphenoxy polyethylene glycol (meth)acrylate, nonylphenoxy polyalkylene glycol (meth)acrylate, and polypropylene glycol mono(meth)acrylate. As urethane compounds, for example, there are urethane compounds obtained by reaction of a diisocyanate compound such as hexamethylene diisocyanate, tolylene diisocyanate, 2,2,4-trimethylhexamethylene diisocyanate or the like and a compound (2-hydroxypropyl acrylate, oligo-propylene glycol monomethacrylate, etc.) having a hydroxyl group and (meth)acryl group in one molecule, and the like. Specifically, there is a reactant (made by NOF CORPORATION, BLEMMER PP1000) of hexamethylene diisocyanate and oligo-propylene glycol monomethacrylate.

Further, in this Embodiment, it is also preferable to contain nitrogen-containing photopolymerizable monomers, as a photopolymerizable radical polymerization-based resin composition forming the resin layer having microwells. Specifically, it is preferable to contain a monomer that is an N-vinyl compound in a range of 5 to 40 percent by weight. Herein, as particularly preferably used monomers that are N-vinyl compounds, there is at least one or more of N-vinylformamide, N-vinylacetamide, N-vinylpyrrolidone and N-vinylcaprolactam. By blending these N-vinyl compounds, it is possible to improve adherence between the resin layer having microwells and the substrate film, and it is made possible to maintain low autofluorescence properties.

Furthermore, by containing the nitrogen-containing photopolymerizable monomer described previously, mold release properties from the mold after polymerization is also good, being preferable.

A content of the nitrogen-containing photopolymerizable monomer is preferably 5 percent by weight or more in order to exert the above-mentioned effect. Further, a content of 40 percent by weight or less is to enable suppression of byproduct of oligomer with a low polymerization degree that is breezed out from the polymer, to also enable suppression of excessive moisture absorption of the resin layer having microwells, to also improve moisture resistance of the microwell film for bioassay of this Embodiment, and is preferable. The content of the nitrogen-containing photopolymerizable monomer is preferably in a range from 15 to 38 percent by weight in terms of above-mentioned improvements in adherence, and is particularly preferably in a range from 25 to 35 percent by weight.

The composition of this Embodiment may contain single-functional monomers together.

Examples thereof are phenoxyethyl acrylate, tetrahydrofurfuryl acrylate, isobornyl acrylate, 2-hydroxyethyl acrylate, 4-hydroxybutyl acrylate, isobutyl acrylate, t-butyl acylate, isooctyl acrylate, 2-methoxyethyl acrylate, methoxy triethylene glycol acrylate, 2-ethoxyethyl acrylate, 3-methoxybuthyl acrylate, ethoxyethyl acrylate, butoxyethyl acrylate, ethoxydiethyl glycol acrylate, 2-hydroxyethyl acrylate, ethyl diglycol acrylate, cyclic trimethylol propane formal monoacrylate, imide acrylate, isoamyl acrylate, ethoxyed succinic acid acrylate, trifluoroethyl acrylate, ω-carboxyl polycaprolactone monoacrylate, benzyl acrylate, methyl phenoxyethyl acrylate, cyclohexyl acrylate, 4-t-butyl cyclohexyl acrylate, caprolactone-modified tetrahydrofurfuryl acrylate, tribromo phenyl acrylate, ethoxyed tribromo phenyl acrylate, 2-phenoxyethyl acrylate, acryloylmorpholine, phenoxy diethylene glycol acrylate, 2-hydroxy-3-phenoxypropyl acrylate, 1,4-cyclohexane dimethanol monoacrylate, 2-(2-ethoxyethoxy)ethyl acrylate, stearyl acrylate, diethylene glycol monobutyl ether acrylate, lauryl acrylate, isodecyl acrylate, 3,3,5-trimethyl cyclohexanol acrylate, isooctyl acrylate, octyl-decyl acrylate, tridecyl acrylate, caprolactone acrylate, ethoxyed (4) nonylphenol acrylate, methoxy polyethylene glycol (350) monoacrylate, methoxy polyethylene glycol (550) monoacrylate and the like, but are not limited thereto. These monomers may be used in a combination of two kinds or more as necessary.

A blending quantity of the above-mentioned photopolymerizable monomer preferably ranges from 10 to 95 percent by weight, and more preferably ranges from 20 to 92 percent by weight, relative to weight of the photosensitive resin composition. In addition, the blending quantity of the photopolymerizable monomer is more preferably in a range of 10 to 80 percent by weight. In this range, the composition has a low viscosity and sufficient cured hardness, and it is possible to obtain the microwell film for bioassay having microwells suitable for the "unimolecular enzyme assay" method by the optical imprint method.

In the case where the fluororesin is contained in the resin layer, when a ratio between a fluorine element concentration (Fs) of the surface of the resin layer and an average fluorine element concentration (Fb) in the resin layer meets the following Equation (2), such a ratio is suitable for the substrate for bioassay as described above.

$1 < (Fs/Fb) \leq 15000$   Equation (2)

By setting the fluorine concentration of the surface (in the vicinity of microwell structure) of the resin layer at the average fluorine concentration of the resin layer or more, by reason of low free energy, the surface of the resin layer develops the surface liquid repellent property, and promotes formation of a minute droplet inside the microwell. This is because when an examination medium is applied onto the microwell film for bioassay, the examination medium enters inside the microwell, but a droplet is separated inside the microwell and the film uppermost surface due to the liquid repellent property of the surface. As a result, the examination medium remains only inside the microwell. Particularly, such a concentration is suitable as the substrate for the "unimolecular enzyme assay" method requiring minute droplets.

On the other hand, a high fluorine concentration of the resin layer reduces adhesion to the substrate, and is not preferable, and therefore, by maintaining free energy high near the substrate, it is possible to maintain higher adhesion.

Particularly, when the ratio is in a range of $20 \leq (Fs/Fb) \leq 200$, the fluorine element concentration (Fs) of the surface portion of the resin layer is sufficiently higher than the average fluorine concentration (Fb) in the resin layer, and it is thereby possible to effectively decrease free energy of the resin layer surface. Further, by lowering the average fluorine concentration (Fb) in the resin layer relatively to the fluorine element concentration (Fs) of the surface portion of the resin layer, the strength of the resin layer itself is improved, while it is possible to maintain free energy high in the vicinity of the substrate in the resin layer, adherence to the substrate is thereby improved, and such a range is preferable.

Further, when the ratio is in a range of $26 \leq (Fs/Fb) \leq 189$, it is possible to further lower free energy of the resin surface, and the range is preferable. Furthermore, when the ratio is in a range of $30 \leq (Fs/Fb) \leq 160$, it is possible to decrease free energy of the resin surface, and to maintain the strength of the resin, and the range is preferable. A range of $31 \leq (Fs/Fb) \leq 155$ is more preferable. A range of $46 \leq (Fs/Fb) \leq 155$ is to enable the above-mentioned effect to be further developed, and is preferable.

In the photosensitive resin composition in this Embodiment, in addition to the above-mentioned photopolymerizable monomer, it is preferable to contain fluorine-containing (meth)acrylate expressed by the following chemical formula (1), and the content is preferably in a range of 0.1 to 20 percent by weight relative to weight of the photosensitive resin composition.

[Chemistry 4]

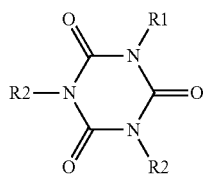

Chemical formula (1)

(In the chemical formula (1), R1 represents the following chemical formula (2), and R2 represents the following chemical formula (3).)

[Chemistry 5]

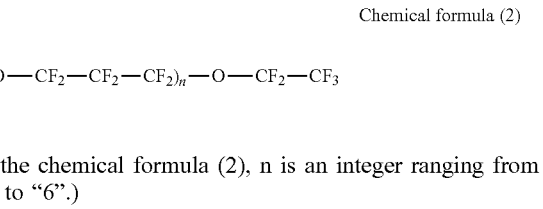

Chemical formula (2)

(In the chemical formula (2), n is an integer ranging from "1" to "6".)

[Chemistry 6]

Chemical formula (3)

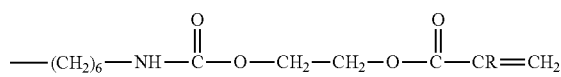

(In the chemical formula (3), R represents H or CH$_3$.)

The content of 0.1 percent by weight or more is excellent in mold release properties and is preferable, and the content of 20 percent by weight or less is excellent in adherence to the substrate and is preferable. Particularly, the content in a range of 0.5 to 10 percent by weight enables compatibility between the mold release property and adherence to the substrate in the light nanoimprint method, and is preferable.

In addition, among the above-mentioned ranges, 0.8 part by weighty or more of the fluorine-containing (meth)acrylate enables the fluorine element concentration (Fs) of the resin layer surface portion (microwell surface) to be increased and is preferable, and 6 parts by weight or less of the fluorine-containing (meth)acrylate lowers the average fluorine element concentration (Fb) in the resin, enables the strength of the microwell of the resin layer and the adherence force of the substrate interface to be increased, and is preferable. Further, a range of 1 part by weight to 6 parts by weight enables free energy of the resin surface to be further decreased, makes minute droplet formation in the microwell good, and is preferable.

The "surface portion of the resin layer" in the present Description indicates a surface portion of the microwell of the resin layer, and in a thickness direction orthogonal to the surface of the resin layer, means a portion in a range from approximately 1% to 10% from the surface side of the resin layer, or a portion in a range from 2 nm to 20 nm. Further, in this Embodiment, the fluorine element concentration (Fs) of the surface portion of the resin layer adopts a value obtained by XPS method described later. In this Embodiment, the fluorine element concentration (Fs) is defined as a measurement value in a depth of several nanometers that is a penetration length of X-ray in the XPS method.

On the other hand, in the present Description, the "average fluorine element concentration (Fb) in the resin" adopts a value calculated from the amount of material prepared, or a value capable of being analyzed from a gas chromatography-mass spectroscopy analyzer (GC-MS). In other words, Fb means a fluorine element concentration contained in the resin constituting the resin layer. For example, in the resin layer comprised of the cured material of the photopolymerizable mixture formed in the shape of a film, a section of a physically peeled resin portion is decomposed by a flask combustion method, and then, is subjected to ion chromatography analysis, and it is thereby possible to identify the average fluorine element concentration (Fb) in the resin.

In the microwell film for bioassay of this Embodiment, it is preferable that an average nitrogen element concentration (Nf) of the resin layer is higher than an average nitrogen element concentration (Ns) of the substrate, and that the substrate has a region with a nitrogen element concentration (Ni) meeting the following equation (1) on the first main surface side provided with the resin layer.

$$Nf > Ni > Ns \quad \text{Equation (1)}$$

Further, on the first main surface side provided with the resin layer, the substrate preferably has a region where the nitrogen element concentration gradually decreases toward the second main surface on the side opposite to the first main surface.

By the nitrogen element concentration (Ni) existing in the direction from the interface (first main surface) between the resin layer having the microwell and the substrate to the backside (second main surface), in other words, existing inside the interface on the substrate side, adhesion is made good between the resin layer having the microwell and the substrate. Particularly, adhesion is made good to a cycloolefin polymer substrate film which is excellent in transparency and the low autofluorescence property, and is suitable as the substrate for bioassay but is low in adhesion to the photosensitive resin composition, and the existence of the nitrone element concentration is preferable.

An explicit mechanism is unknown about the fact that when the distribution of the nitrogen element concentration (Ni) as described above exists inside the interface on the substrate side, adhesion is good to the substrate, particularly, the cycloolefin polymer substrate film, but is estimated as described below.

In other words, it is considered that the nitrogen-containing photopolymerizable monomer penetrates inside the substrate from the interface with the resin layer and is polymerized inside the substrate, and that molecular chain networks are thereby formed with the resin layer on the surface to generate strong interface adhesion force. By detailed studies of the inventors, it is found out that penetration force of the nitrogen-containing photopolymerizable monomer is strong and generates strong adhesion force.

A layer thickness where the nitrogen element concentration (Ni) gradually decreases is preferably in a range of 1 nm to 100 nm to develop good adhesion, more preferably in a range of 1 nm to 500 nm to enhance adhesion reinforcement curing by curing of the nitrogen-containing photopolymerizable monomer, and more preferably in a range of 1 nm to 2000 nm because haze due to penetration of the nitrogen-containing photopolymerizable monomer does not exist, and the adhesion is further enhanced. Thus, the lower limit value of the layer thickens where the nitrogen element concentration (Ni) gradually decreases is set at 1 nm, more preferably 10 nm or more to develop the adhesion, and further preferably 50 nm or more to develop stable adhesion.

Further, in the present Description, the "average nitrogen element concentration (Nf) in the resin having the microwell" adopts a value calculated from the amount of material prepared, or a value capable of being analyzed from the gas chromatography-mass spectroscopy analyzer (GC-MS). In other words, Nf means a nitrogen element concentration contained in the resin constituting the resin layer. For example, in the resin layer comprised of the cured material of the photopolymerizable mixture formed in the shape of a film, a section of a physically peeled resin portion is decomposed by the flask combustion method, and then, is subjected to ion chromatography analysis, and it is thereby possible to identify the average nitrogen element concentration (Nf) in the resin.

Furthermore, similarly, in the present Description, the "average nitrogen element concentration (Ns) of the substrate" adopts a value capable of being analyzed from the gas chromatography-mass spectroscopy analyzer (GC-MS). In other words, Ns means a nitrogen element concentration contained in the substrate. For example, a section physically peeled off from the substrate is decomposed by the flask combustion method, and then, is subjected to ion chromatography analysis, and it is thereby possible to identify the average nitrogen element concentration (Ns) in the substrate.

Still furthermore, in the present Description, with respect to the nitrogen element concentration (Ni) existing in the direction from the interface between the resin layer having the microwell and the substrate to the second main surface (backside), in cross section cut in the direction perpendicular to the main surface, Ni adopts a value obtained by measuring a nitrogen element concentration of the interface between both the resin layer having the microwell and the substrate. As a measurement method, there are EDX (energy-dispersive X-ray spectroscopy) and EELS (electron energy loss spectroscopy).

Moreover, there is also a method of cutting the interface by an extremely low angle oblique cut method with about 2 degrees to 5 degrees, and measuring the exposed interface vicinity by TOF-SIMS (Time of flight-secondary ion mass spectrometry). According to this method, it is possible to acquire information obtained by enlarging the nitrogen element concentration in the vicinity of the interface in the thickness direction, it is thereby possible to measure the nitrogen element concentration in the depth direction with accuracy, and the method is preferable.

In addition to the above-mentioned photopolymerizable monomer, the photopolymerizable radical polymerization-based resin in this Embodiment preferably contains a photopolymerizable oligomer, and is capable of using oligomers having ethyleny unsaturated double bonds. Examples thereof are aromatic urethane oligomers, aliphatic urethane oligomers, epoxy acrylate oligomers, polyester acrylate oligomers, aliphatic urethane acrylate oligomer and other specific oligomers.

Commercial products thereof are UV-2000B, UV-2750B, UV-3000B, UV-3010B, UV-3200B, UV-3300B, UV-3700B, UV-6640B, UV-8630B, UV-7000B, UV-7610B, UV-1700B, UV-7630B, UV-6300B, UV-6640B, UV-7550B, UV-7600B, UV-7605B, UV-7610B, UV-7630B, UV-7640B, UV-7650B, UT-5449, UT-5454 made by The Nippon Synthetic Chemical Industry Co., Ltd., CN902, CN902J75, CN929, CN940, CN944, CN944B85, CN959, CN961E75, CN961H81, CN962, CN963, CN963A80, CN963B80, CN963E75, CN963E80, CN963J85, CN964, CN965, CN965A80, CN966, CN966A80, CN966B85, CN966H90, CN966J75, CN968, CN969, CN970, CN970A60, CN970E60, CN971, CN971A80, CN971J75, CN972, CN973, CN973A80, CN973H85, CN973J75, CN975, CN977, CN977C70, CN978, CN980, CN981, CN981A75, CN981B88, CN982, CN982A75, CN982B88, CN982E75, CN983, CN984, CN985, CN985B88, CN986, CN989, CN991, CN992, CN994, CN996, CN997, CN999, CN9001, CN9002, CN9004, CN9005, CN9006, CN9007, CN9008, CN9009, CN9010, CN9011, CN9013, CN9018, CN9019, CN9024, CN9025, CN9026, CN9028, CN9029, CN9030, CN9060, CN9165, CN9167, CN9178, CN9290, CN9782, CN9783, CN9788, CN9893 made by Sartomer Company, EBECRYL (Registered Trademark) 210, EBECRYL220, EBECRYL230, EBECRYL270, KRM8200, EBECRYL5129, EBECRYL8210, EBECRYL8301, EBECRYL8804, EBECRYL8807, EBECRYL9260, KRM7735, KRM8296, KRM8452, EBECRYL4858, EBECRYL8402, EBECRYL9270, EBECRYL8311, EBECRYL8701 made by DAICEL-CYTEC Co., Ltd. and so on, and it is also possible to use these compounds together.

Further, it is also possible to use oligomers obtained by synthesis alone or in combination.

A blending quantity of the above-mentioned monomer is preferably in a range of 10 to 80 percent by weight, and more preferably in a range of 20 to 80 percent by weight, relative to weight of the photosensitive resin compound. In the range, it is possible to suppress thickness variations in the obtained cured material in the light nanoimprint method, and to obtain the microwell film for bioassay having microwells suitable for the "unimolecular enzyme assay" method by the light nanoimprint method.

<Photopolymerization Initiator>

The photopolymerization initiator contained in the photopolymerizable radical polymerization-based resin in this Embodiment is not particularly limited, it is possible to use publicly known photopolymerization initiators, and it is preferable that light absorption is low at each of wavelengths of 350 nm to 800 nm. The photopolymerization initiator initiates the radical reaction or ion reaction by light, and the photopolymerization initiator initiating the radical reaction is preferable. As the photopolymerization initiator, there are the following photopolymerization initiators.

As the photopolymerization initiator, there are photopolymerization initiators (hereinafter, also referred to as "oxime-based photopolymerization initiator") having oxime ester structure, photopolymerization initiators (hereinafter, also referred to as "α-aminoalkylphenon-based photopolymerization initiator") having α-aminoalkylphenon structure, photopolymerization initiators (hereinafter, also referred to as "α-hydroxyalkylphenon-based polymerization initiator") having α-hydroxyalkylphenon structure, photopolymerization initiators (hereinafter, also referred to as "acylphosphine oxide-based photopolymerization initiator") having acylphosphine oxide structure, photopolymerization initiators (hereinafter, also referred to as "N-phenyl glycinin-based photopolymerization initiator") having N-phenyl glycinin structure, and the like.

Among the photopolymerization initiators, the α-hydroxyalkylphenon-based polymerization initiator is particularly preferable, because it is easy to set the absorption coefficient at each of wavelengths of 350 nm to 800 nm at 0.01 $\mu m^{-1}$ or less after curing, and the absorption coefficient at the wavelength of 300 nm is 0.02 $\mu m^{-1}$ or less and is the maximum value among respective absorption coefficients at wavelengths of 300 nm to 800 nm.

As commercial products of the photopolymerization initiator, there are 1-[4-(phenylthio)]-1,2-octanedion-2-(O-benzoyl oxime) (Brand name: IRGACURE (Registered Trademark) OXE-01, made by BASF Company), 1-[9-ethyl-6-(2-methylbenzoyl)-9H-carbazole-3-yl]ethanone-1-(O-acetyl oxime) (Brand name: IRGACURE (Registered Trademark) OXE-02, made by BASF Company), 2-(dimethylamino)-2-[(4-methylphenyl)methyl]-1-[4-(4-morpholinyl)phenyl]-1-butanone (Brand name: Omnirad (Registered Trademark) 379EG, made by IGM Resins B.V. Company), 2-methyl-1-(4-methythiophenyl)-2-morpholino-propane-1-one (Brand name: Omnirad 907, made by IGM Resins B.V. Company), 2-hydroxy-1-{4-[4-(2-hydroxy-2-methyl-propionyl)-benzyl]phenyl}-2-methyl-propane-1-one (Brand name: Omnirad 127, made by IGM Resins B.V. Company), 2-benzyl-2-dimethylamino-1-(4-morpholino-phenyl)-butanone-1 (Brand name: Omnirad 369, made by IGM Resins B.V. Company), 2-hydroxy-2-methyl-1-phenyl-propane-1-one (Brand name: Omnirad 1173, made by IGM Resins B.V. Company), 1-hydroxycyclohexylphenylketone (Brand name: Omnirad 184, made by IGM Resins B.V. Company), 2,2-dimethoxy-1,2-diphenylethane-1-one (Brand name: Omnirad 651, made by IGM Resins B.V.

Company), oxime ester-based compound (Brand name: Lunar 6, made by DKSH Japan) and the like.

A content of the above-mentioned photopolymerization initiator is preferably in a range of 0.5 to 10 percent by weight, and more preferably in a range of 1.0 to 5 percent by weight, relative to weight of the photosensitive resin composition. In the range, it is easy to set the absorption coefficient at each of wavelengths of 350 nm to 800 nm at 0.01 $\mu m^{-1}$ or less after curing, and it is possible to obtain the microwell film for bioassay of this Embodiment.

<<Method of Manufacturing the Microwell Film for Bioassay>>

The method of manufacturing the microwell film for bioassay of this Embodiment is not particularly limited, and it is possible to select a manufacturing method by transfer from a predetermined master mold by the optical imprint method.

The master mold is provided with a reverse shape pattern of desired microwells on its surface, among materials are quartz glass, UV-transparent glass, sapphire, diamond, silicone materials such as polydimethyl siloxane, fluororesin, silicon, $SiO_2$, Al, SiC, nickel, chrome and the like, and each material may be layered to be a composite material. Mold release treatment may be performed to improve mold release properties in transferring.

Particularly, by applying the mold release treatment to the master mold, free energy decreases on the master mold surface. Therefore, by transferring in a state in which the average fluorine concentration (Fb) in the resin layer is kept low, the fluorine-containing (meth)acrylate according to this Embodiment is effectively segregated to the master mold surface so as to lower energy of the entire system comprised of master mold/photosensitive resin mixture/substrate, and it is thereby possible to increase Fs/Fb. Therefore, as well as the mold release property in transferring, the obtained microwell film is suitable as the substrate for bioassay.

In addition, from the viewpoint of durability of the mold release treatment to the master mold, as a mold release agent, silane coupling-based mold release agents are preferable. Examples of commercially available mold release agents are OPTOOL DSX, DURASURF HD-1100, HD2100 made by Daikin Industries, Ltd., and Novec made by Sumitomo 3M Limited.

The method of manufacturing the microwell film for bioassay of this Embodiment will be described below.

<Process 1>

Process 1: The photosensitive resin composition is applied onto the substrate or master mold. Among methods for applying the resin composition are flow casting method, potting method, spin coat method, roller coat method, bar coat method, cast method, dip coat method, die coat method, Langmuir-Blodgett method, spray coat method, air knife method, flow coat method, curtain coat method and the like. A coating thickness of the photocurable resin composition preferably ranges from 50 nm to 5 mm, more preferably ranges from 100 nm to 200 μm, and further preferably 100 nm to 100 μm.

When the substrate is larger than the master mold, the resin composition may be applied to the entire substrate surface, or may be applied to a part of the substrate so that the resin composition exists only in a range for embossing the master mold. Further, the resin composition may be applied to the master mold side.

After coating the substrate with the resin composition, by prebaking, it is possible to remove a solvent in the case of containing the solvent, or it is possible to promote surface segregation of internal fluorine-containing polymerizable (meth)acrylate. The fluorine-containing polymerizable (meth)acrylate is preferably fluorine-containing polymerizable (meth)acrylates of Chemical formula (1) described above. By segregating the internal fluorine-containing polymerizable (meth)acrylate to the surface, in pressing the master mold, the fluorine-containing polymerizable (meth)acrylate is efficiently filled inside the fine structure of the master mold, it is possible to not only suppress deterioration of the master mold, but also to significantly improve the value Fs/Fb obtained by dividing the surface fluorine element concentration (Fs) of the obtained resin layer by the bulk fluorine element concentration (Fb), and to improve the mold release property. The temperature preferably ranges from 25° C. to 120° C., more preferably ranges from 40° C. to 105° C., further preferably ranges from 50° C. to 105° C., and most preferably ranges from 60° C. to 105° C. The prebake time preferably ranges from 30 seconds to 30 minutes, more preferably ranges from 1 minute to 15 minutes, and further preferably ranges from 3 minutes to 10 minutes.

It is preferable to apply treatment for improving adhesion between the substrate and the resin composition. For example, it is preferable to apply, to the surface of the substrate to adhere, easy adhesion coating, primer treatment, corona treatment, plasm treatment, UV/ozone treatment, high-energy ray irradiation treatment, surface roughening treatment, multi-porous treatment and the like for chemical bonding with the resin composition and physical coupling such as penetration.

<Process 2>

Process 2: Penetration Process of the Photosensitive Resin Composition into the Substrate After coating the substrate with the resin composition, by providing the penetration process of the photosensitive resin composition into the substrate, adhesion to the cured resin composition is improved, and such a process is preferable. In the penetration process in this Embodiment, it is enough that the resin composition slightly penetrates inside in the vicinity of the substrate surface, and for example, there is a method of leaving for a predetermined time after coating the substrate with the resin composition. As conditions of the penetration process, the temperature preferably ranges from 15° C. to 120° C., more preferably ranges from 20° C. to 105° C., and further preferably ranges from 25° C. to 105° C. The time of the penetration process preferably ranges from 1 minute to 30 minutes, more preferably ranges from 2 minutes to 15 minutes because adhesion is good after curing the photosensitive resin composition, and further preferably ranges from 3 minutes to 10 minutes because it is possible to further suppress increases in haze of the substrate interface. Particularly, by applying the photosensitive resin composition containing the nitrogen-containing photopolymerizable monomer as the photopolymerizable monomer to the substrate to penetrate, it is possible to effectively improve adhesion force in the interface between the substrate and the resin layer.

<Process 3>

Process 3: Process of Pressing the Photosensitive Resin Composition Between the Substrate and the Master Mold In order for a bubble not to enter, it is preferable to gently apply the substrate with high flexibility onto the master mold from the end and press under a certain pressure. The press pressure in pressing preferably ranges from above 0 MPa to 10 MPa, more preferably ranges from 0.01 MPa to 5 MPa, and further preferably ranges from 0.01 MPa to 1 MPa.

<Process 4>
Process 4: Process of Curing the Photocurable Resin Composition by Exposure to Light and Obtaining the Cured Material In the case where light transmittance of the master mold is low, it is preferable to perform exposure from the substrate side. On the other hand, in the case where transmittance of the master mold is high to light with UV wavelengths, for example, in the case of synthetic quartz materials, it is preferable to perform exposure from at least one side face on the substrate side or the master mold side, and it is more preferable to perform exposure from both faces on the substrate side and the master mold side. In order to prevent polymerization from being inhibited by oxygen, an atmosphere in exposure may be an atmosphere of nitrogen, or an atmosphere of argon.

Among preferable exposure light sources to use are metal halide lamps, high pressure mercury lamps, chemical lamps and UV-LEDs. From the viewpoint of suppression of heating in long-time exposure, it is preferable to use a filter (including a band-pass filter) for cutting wavelengths longer than visible wavelengths. The integral amount of light is preferably 300 mJ/cm$^2$ or more at a wavelength of 365 nm, preferably 800 mJ/cm$^2$ or more for the purpose of obtaining the cured material (E) with high reactivity, more preferably 800 mJ/cm$^2$~6000 mJ/cm$^2$, and particularly preferably 800 mJ/cm$^2$~3000 mJ/cm$^2$ to prevent resin deterioration properties by light.

Without depending on the thickness of the cured material, all-light transmittances at 350 nm to 450 nm are preferably 50% or more, and more preferably 70% or more to perform efficient light reaction. When the thickness of the cured material ranges from above 0 nm to 50 μm, all-light transmittances at 350 nm to 450 nm are preferably 50% or more, and more preferably 70% or more.

<Process 5>
Process 5: Process of Peeling Off the Cured Material from the Master Mold In the case where the master mold is flexible, it is preferable to peel from at least one of the mold surface side and the substrate surface side at a certain velocity. As a peeling method, linear peeling is preferable. For example, in the case where materials of the master mold are high in rigidity, particularly, in the case of inorganic materials, in peeling from the master mold side, a peeling area is partially wide by face peeling, and there is the risk that the cured material is broken. Accordingly, it is preferable to peel from the substrate side with flexibility. As the peeling velocity, it is preferable that linear peeling is performed at a certain velocity ranging from above 0 m/min to 5 m/min from a particular direction, from the viewpoint of reducing the breakage risk of the cured material.

Further, it is preferable to apply heating treatment at the time between after curing and before peeling. By applying the heating treatment in this process, it is possible to decrease non-reacted groups, mold release is made easy, and further, durability of the master mold is improved. The temperature preferably ranges from 50° C. to 120° C., more preferably ranges from 50° C. to 105° C., and further preferably ranges from 60° C. to 105° C. The heating time preferably ranges from 30 seconds to 30 minutes, more preferably ranges from 30 seconds to 15 minutes, and further preferably ranges from 1 minute to 10 minutes.

On the other hand, the heating treatment may be performed after peeling. By performing the heating treatment after peeling, the reaction of non-reacted groups is promoted, and such heating treatment is preferable. The temperature preferably ranges from 50° C. to 120° C., more preferably ranges from 50° C. to 105° C., and further preferably ranges from 60° C. to 105° C. The heating time preferably ranges from 30 seconds to 30 minutes, more preferably ranges from 30 seconds to 15 minutes, and further preferably ranges from 1 minute to 10 minutes.

EXAMPLES

The present invention will be described below in more detail based on Examples performed to clarify the effect of the present invention. In addition, the present invention is not limited by the following Examples at all.

[Residual Film Thickness Measurement]

The thickness of the resin layer of the prepared microwell film and the thickness of the thinnest portion of the well bottom were measured by scanning electron microscope (hereinafter, SEM) observation. First, after cutting samples to a proper size, the sample was cut in section at room temperature, and was placed on a sample mount. Next, an observation surface was coated with Os to the extent of 2 nm, and was made a sample for microscopic examination. The used apparatus and microscopic examination conditions will be described below.

Apparatus; HITACHI s-5500
Acceleration voltage; 10 kV
Mode; Normal

[Fluorine Element Concentration Measurement]

The surface fluorine element concentration of the resin layer was measured by X-ray photoelectron spectroscopy (hereinafter, XPS). Since a penetration length of X ray to the sample surface in XPS is several nanometers and extremely shallow, a measurement value of XPS was adopted as a fluorine element concentration (Fs) of the resin layer surface. The microwell film was cut to small pieces about 2 mm square, and the piece was covered with a 1 mm×2 mm slot type mask, and was subjected to XPS measurement on the following conditions.

XPS measurement conditions
Used apparatus; Thermo Fisher ESCALAB 250
Excitation source; mono. Alkα 15kV×10 mA
Analysis size; about 1 mm (the shape is an ellipse)
Capture region
  Survey scan; 0~1,100 eV
  Narrow scan; F 1s, C 1s, O 1s, N 1s
Pass energy
  Survey scan; 100 eV
  Narrow scan; 20 eV On the other hand, to measure the average fluorine element concentration (Fb) in the resin constituting the resin layer of the microwell film, a physically peeled cut piece was decomposed by the flask combustion method, and then, was subjected to ion chromatography analysis, and the average fluorine element concentration (Fb) in the resin layer was measured.

[Nitrogen Element Concentration Measurement]

The nitrogen element concentration in a cross-sectional direction perpendicular to the main surface of the microwell film was obtained by preparing a cut surface with a microtome, while inclining 2 degrees to 5 degrees from a parallel with the surface, and measuring an exposed interface layer by TOF-SIMS (Time of flight-secondary ion mass spectrometry). In addition, in order to remove ingredient pollution from a blade of the microtome, the cur surface was cleaned by GCIB sputter.

TOF-SIMS Measurement Conditions
  Used apparatus: nano TOF (made ULVAC-PHI, Inc.)
  Primary ion: $Bi_3^{++}$
  Acceleration voltage: 30 kV
  Current value: about 0.2 nA (as DC)
  Bunching: non
  Analysis area: 50 mm×50 mm
  Cumulative time: 20 minutes
  Detection ion: negative ion
  Neutralization: electron gun
[Autofluorescence Property]

The autofluorescence property of the microwell film was measured on the following conditions, and a fluorescence amount was evaluated as a corresponding standard reference material concentration from beforehand prepared calibration curves of the standard reference material.
  Used apparatus: Synergy HTX Plate Reader (made by BioTek Instruments, Inc.)
  Light source: Tungsten lamp
  Excitation light filter: 340 nm~380 nm
  Fluorescence filter: 440 nm~480 nm
  Standard reference material: Hoechst 33342 (made by DOJIN KAGAKUSYA)
  Calibration curves were prepared in 0 μg~0.3125 μg.
[Absorption Coefficient]

The "absorption coefficient" was obtained by the following equation (6).

$$\text{Absorption coefficient} = \text{absorbance}/\text{film thickness (μm)} \quad \text{Equation (6)}$$

In the absorption coefficient of the resin layer, the absorbance and film thickness are "absorbance of the resin layer and film thickness of the resin layer", and in the absorption coefficient of the substrate, the absorbance and film thickness are "absorbance of the substrate and film thickness of the substrate".

Further, the absorbance is calculated according to the following equation (7).

$$\text{Absorbance} = -\log(\text{light transmittance}) \quad \text{Equation (7)}$$

The light transmittance is capable of being obtained by measuring with a general spectrophotometer, and in the experiments, Spectrophotometer UV-2500 (made by Shimadzu Corporation) was used.

Example 1

Mold release treatment was applied to a plate-shaped mold made of nickel with column-shaped convex portions each with ϕ of 4 μm and height of 4 μm trigonally arranged with a pitch of 6 μm, using Durasurf (Registered Trademark) 2101Z made by HARVES Co., Ltd.

N-vinyl pyrolidone, urethane oligomer (made by SARTOMER Company CN991) and Omnirad 184 (made by IGM Resins B.V. Company) were mixed in a ratio of 50:50:5 in parts by weight, and the mixture was dropped onto a fine concavo-convex structure surface of the mold.

Next, the mixed solution was sandwiched by a cyclic olefin resin film (made by JSR Corporation, ARTON (Registered Trademark), t188 μm) with surface plasm treatment beforehand applied, and concurrently therewith, the resultant was drawn using a hand roller. After performing UV exposure from the film surface side, the resin layer cured to be integrated with the cyclic olefin resin film was peeled off from the mold to obtain the microwell film for bioassay with the resin layer and the substrate integrated.

On the obtained microwell film surface, cylindrical wells each with ϕ of 4 μm and depth of 4 μm were trigonally arranged with a pitch of 6 μm, a thickness of the resin layer was 4.2 μm and uniform including the well depth, a thickness of the thinnest portion of the well bottom was (=) 0.2 μm, and the entire film thickness was 192 μm and uniform. Since the film was thin and uniform, in the "unimolecular enzyme assay" method, it was expected that temperature control by a temperature control plate is easy to perform, variations in temperature control are suppressed, and that the edge effect is suppressed.

Among the absorption coefficients at wavelengths of 350 nm to 800 nm of the cyclic olefin resin film and the resin layer of the obtained microwell film for bioassay, the maximum absorption coefficients were obtained at the wavelength of 350 nm, and were 0.001 $\mu m^{-1}$ and 0.005 $\mu m^{-1}$, respectively.

Further, among the absorption coefficients at wavelengths of 300 nm to 800 nm of the resin layer of the microwell film, the maximum absorption coefficient was obtained at the wavelength of 300 nm, and was 0.015 $\mu m^{-1}$.

Furthermore, the autofluorescence property was equivalent to 0.005 μg of Hoechst 33342.

Example 2

The mold release treatment was applied to the plate-shaped mold as in Example 1, using Durasurf 2101Z made by HARVES Co., Ltd.

The fluorine-containing acrylate (made by Daikin industries, Ltd. OPTOOL DAC HP, solid content 20%), trimethylol propane triacrylate (made by TOAGOSEI CO., LTD. M350), urethane oligomer (made by SARTOMER Company CN991) and Omnirad 184 (made by IGM Resins B.V. Company) were mixed in a ratio of 17:50:50:5 in parts by weight, and the mixture was dropped onto the fine concavo-convex structure surface of the mold.

Next, the mixed solution was sandwiched by the cyclic olefin resin film (made by JSR Corporation, ARTON (Registered Trademark), t188 μm) with surface plasm treatment beforehand applied, and concurrently therewith, the resultant was drawn using a hand roller. After performing UV exposure from the film surface side, the resin layer cured to be integrated with the cyclic olefin resin film was peeled off from the mold to obtain the microwell film for bioassay with the resin layer and the substrate integrated.

On the obtained microwell film surface, cylindrical wells each with ϕ of 4 μm and depth of 4 μm were trigonally arranged with a pitch of 6 μm, a thickness of the resin layer was 4.2 μm and uniform including the well depth, a thickness of the thinnest portion of the well bottom was (=) 0.2 μm, and the entire film thickness was 192 μm and uniform. Since the film was thin and uniform, in the "unimolecular enzyme assay" method, it was expected that temperature control by a temperature control plate is easy to perform, variations in temperature control are suppressed, and that the edge effect is suppressed.

Among the absorption coefficients at wavelengths of 350 nm to 800 nm of the cyclic olefin resin film and the resin layer of the obtained microwell film for bioassay, the maximum absorption coefficients were obtained at the wavelength of 350 nm, and were 0.001 $\mu m^{-1}$ and 0.008 $\mu m^{-1}$, respectively.

Further, among the absorption coefficients at wavelengths of 300 nm to 800 nm of the resin layer of the microwell film, the maximum absorption coefficient was obtained at the wavelength of 300 nm, and was 0.02 $\mu m^{-1}$.

Furthermore, the autofluorescence property was equivalent to 0.006 μg of Hoechst 33342.

Still furthermore, the obtained microwell film surface was measured by XPS, and the ratio Fs/Fb between the fluorine element concentration (Fs) of the surface and the average fluorine element concentration (Fb) in the resin was "48". The surface liquid repellent property was high, and the resultant was suitable as a substrate in the "unimolecular enzyme assay" method.

Example 3

The mold release treatment was applied to the plate-shaped mold as in Example 1, using Durasurf 2101Z made by HARVES Co., Ltd.

N-vinyl pyrolidone, urethane oligomer (made by SARTOMER Company CN991), trimethylol propane triacrylate (made by TOAGOSEI CO., LTD. M350) and Omnirad 184 (made by IGM Resins B.V. Company) were mixed in a ratio of 33:20:47:5 in parts by weight.

Next, the photosensitive resin mixture was dropped onto a cyclic olefin resin film (made by ZEON CORPORATION, Zeonor Film (Registered Trademark) t188 μm) with surface plasm treatment beforehand applied, and was uniformly applied and spread with a spin coater. Subsequently, the resultant was let stand for 5 minutes to be the penetration process for the photosensitive resin mixture to penetrate the substrate.

Next, using the mold having the fine concavo-convex structure on its surface as in Example 1, the photosensitive resin mixture was dropped onto the fine concavo-convex structure surface of the mold.

Next, the mixed solution was sandwiched by the cyclic olefin resin film (made by ZEON CORPORATION, Zeonor Film ZF-14, t188 μm) with surface plasm treatment beforehand applied, and concurrently therewith, the resultant was drawn using a hand roller. After performing UV exposure from the film surface side, the resin layer cured to be integrated with the cyclic olefin resin film was peeled off from the mold to obtain the microwell film for bioassay with the resin layer and the substrate integrated.

On the obtained microwell film surface, cylindrical wells each with ϕ of 4 μm and depth of 4 μm were trigonally arranged with a pitch of 6 μm, a thickness of the resin layer was 4.2 μm and uniform including the well depth, a thickness of the thinnest portion of the well bottom was (=) 0.2 μm, and the entire film thickness was 192 μm and uniform. Since the film was thin and uniform, in the "unimolecular enzyme assay" method, it was expected that temperature control by a temperature control plate is easy to perform, variations in temperature control are suppressed, and that the edge effect is suppressed.

Among the absorption coefficients at wavelengths of 350 nm to 800 nm of the cyclic olefin resin film and the resin layer of the obtained microwell film for bioassay, the maximum absorption coefficients were obtained at the wavelength of 350 nm, and were 0.0002 μm$^{-1}$ and 0.003 μm$^{-1}$, respectively.

Further, among the absorption coefficients at wavelengths of 300 nm to 800 nm of the resin layer of the microwell film, the maximum absorption coefficient was obtained at the wavelength of 300 nm, and was 0.005 μm$^{-1}$.

Furthermore, the autofluorescence property was equivalent to 0.0025 μg of Hoechst 33342, exhibited a low autofluorescence property, and was suitable as the microwell film for bioassay. Still furthermore, adhesion was good between the surface resin having the fine concavo-convex structure and the substrate film.

Figure 4:
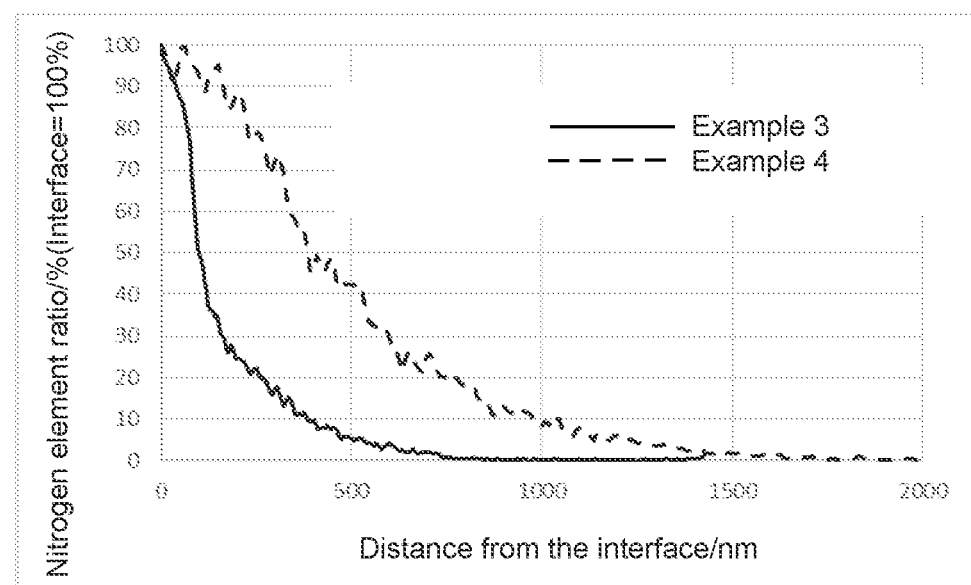
FIG. 4 is a graph of measurement results of nitrogen element concentration distributions in a direction perpendicular to a main surface of the microwell film for bioassay in the Examples.

Moreover, the nitrogen element concentration was measured in the direction perpendicular to the main surface of the nitrogen element concentration of the obtained microwell film for bioassay (FIG. 4). FIG. 4 shows the nitrogen element concentration ratio in the substrate with respect to the distance from the interface with the substrate, when the nitrogen element concentration of the resin layer of the microwell film was set at 100%.

The cyclic cycloolefin resin film used as the substrate originally contains few nitrogen elements, and the average nitrogen element concentration (Ns) in the substrate was almost "0". However, nitrogen elements penetrated the surface of the cyclic cycloolefin resin film, and when the nitrogen element concentration (Nf) in the photocurable resin of the surface having the fine concavo-convex structure was set at 100%, the nitrogen element concentration (Ni) in a position of 532 nm inside the substrate from the interface between the photocurable resin layer and the cyclic olefin resin film was 5%. By this means, it was understood meeting Nf>Ni>Ns.

Example 4

Using the plate-shaped mold as in Example 1, the microwell film for bioassay was obtained using the Zeonor Film as the substrate by the method as in Example 3 except that N-vinyl pyrolidone, urethane oligomer (made by SARTOMER Company CN991), trimethylol propane triacrylate (made by TOAGOSEI CO., LTD. M350) and Omnirad 184 (made by IGM Resins B.V. Company) were mixed in a ratio of 33:10:57:5 in parts by weight.

On the obtained microwell film surface, cylindrical wells each with ϕ of 4 μm and depth of 4 μm were trigonally arranged with a pitch of 6 μm, a thickness of the resin layer was 4.2 μm and uniform including the well depth, a thickness of the thinnest portion of the well bottom was (=) 0.1 μm, and the entire film thickness was 192 μm and uniform. Since the film was thin and uniform, in the "unimolecular enzyme assay" method, it was expected that temperature control by a temperature control plate is easy to perform, variations in temperature control are suppressed, and that the edge effect is suppressed.

Among the absorption coefficients at wavelengths of 350 nm to 800 nm of the cyclic olefin resin film and the resin layer of the obtained microwell film for bioassay, the maximum absorption coefficients were obtained at the wavelength of 350 nm, and were 0.0002 μm$^{-1}$ and 0.0004 μm$^{-1}$, respectively.

Further, among the absorption coefficients at wavelengths of 300 nm to 800 nm of the resin layer of the microwell film, the maximum absorption coefficient was obtained at the wavelength of 300 nm, and was 0.0007 μm$^{-1}$.

Furthermore, the autofluorescence property was equivalent to 0.001 μg of Hoechst 33342, exhibited a low autofluorescence property, and was suitable as the microwell film for bioassay. Still furthermore, adhesion was good between the surface resin having the fine concavo-convex structure and the substrate film.

Moreover, the nitrogen element concentration was measured in the direction perpendicular to the main surface of the nitrogen element concentration of the obtained microwell film for bioassay (FIG. 4). FIG. 4 shows the nitrogen element concentration ratio in the substrate with respect to the distance from the interface with the substrate, when the nitrogen element concentration of the resin layer of the microwell film was set at 100%.

The cyclic cycloolefin resin film used as the substrate originally contains few nitrogen elements, and the average nitrogen element concentration (Ns) in the substrate was almost "0". However, nitrogen elements penetrated the surface of the cyclic cycloolefin resin film, and when the nitrogen element concentration (Nf) in the photocurable resin of the surface having the fine concavo-convex structure was set at 100%, the nitrogen element concentration (Ni) in a position of 1188 nm inside the substrate from the interface between the photocurable resin and the cyclic olefin resin film was 5%. By this means, it was understood meeting Nf>Ni>Ns.

Comparative Example 1

The mold release treatment was applied to the plate-shaped mold as in Example 1, using Durasurf 2101Z made by HARVES Co., Ltd.

The fluorine-containing acrylate (made by Daikin Industries, Ltd. OPTOOL (Registered Trademark) DAC HP, solid content 20%), trimethylol propane triacrylate (made by TOAGOSEI CO., LTD. M350), urethane oligomer (made by SARTOMER Company CN991), Omnirad 184 (made by IGM Resins B.V. Company), and Omnirad 369 (made by IGM Resins B.V. Company) were mixed in a ratio of 17:50:50:5:2 in parts by weight, and the mixture was dropped onto the fine concavo-convex structure surface of the mold.

Next, the mixed solution was sandwiched by a PET film (made by TOYOBO CO., LTD. COSMOSHINE A4100, t188 μm), and concurrently therewith, the resultant was drawn using a hand roller. After performing UV exposure from the film surface side, the mold and film were peeled to obtain a microwell film for bioassay.

On the obtained microwell film surface, cylindrical wells each with φ of 4 μm and depth of 4 μm were trigonally arranged with a pitch of 6 μm, a thickness of the resin layer was 4.2 μm and uniform including the well depth, a thickness of the thinnest portion of the well bottom was (=) 0.2 μm, and the entire film thickness was 192 μm and uniform.

Among the absorption coefficients at wavelengths of 350 nm to 800 nm of the PET film and the resin layer of the obtained microwell film for bioassay, the maximum absorption coefficients were obtained at the wavelength of 350 nm, and were 0.002 μm$^{-1}$ and 0.07 μm$^{-1}$, respectively.

Further, light of 300 nm did not transmit, and it was not possible to measure the absorption coefficient.

Furthermore, the autofluorescence property was equivalent to 0.22 μg of Hoechst 33342. Since the autofluorescence property was strong, it was not possible to separate from fluorescence of a marker, it was thereby not possible to detect the marker, and the film was not suitable for the "unimolecular enzyme assay" method.

Comparative Example 2

An injection molding mold provided with a concavo-convex pattern as in Example 1 was prepared, and by injection molding, a well plate was formed, using a COP resin (made by JSR Corporation ARTON F4520). As in Example 1, as a surface pattern of the injection resin layer, cylindrical wells each with surface φ of 4 μm and depth of 4 μm were trigonally arranged with a pitch of 6 μm, and an entire film thickness was 400 μm and thick.

Since the film was thick, in the "unimolecular enzyme assay" method, it was expected that temperature control by a temperature control plate is hard to perform, and that the occurrence of the edge effect is assumed.

Further, the autofluorescence property was equivalent to 0.01 μg of Hoechst 33342.

Comparative Example 3

The injection molding mold as in Comparative Example 2 was prepared, and by injection molding, a well plate was formed, using a COP resin (made by ZEON CORPORATION ZEONOR 1020R). As in Example 1, as a surface pattern, cylindrical wells each with surface φ of 4 μm and depth of 4 μm were trigonally arranged with a pitch of 6 μm, and an entire film thickness was 300 μm and thick.

Since the film was thick, in the "unimolecular enzyme assay" method, it was expected that temperature control by a temperature control plate is hard to perform, and that the occurrence of the edge effect is assumed.

Further, the autofluorescence property was equivalent to 0.004 μg of Hoechst 33342.

Materials, absorption coefficients, effects so on of Examples 1 to 4 and Comparative Examples 1 to 3 were summarized below in Table 1.

As shown in Table 1, in each of Examples 1 to 4, the absorption coefficient of the resin layer at each of wavelengths of 350 nm to 800 nm was 0.01 μm$^{-1}$ or less. In addition, in each of resins forming substrates used in samples, the absorption coefficient at each of wavelengths of 350 nm to 800 nm was 0.01 μm$^{-1}$ or less, and the absorption coefficient at the wavelength of 300 nm was 0.02 μm$^{-1}$ or less. Then, in each of the Examples, it was possible to obtain low autofluorescence properties equal to or lower than in conventional bioassay plates by Comparative Examples 2 and 3.

TABLE 1

| | Sample | Example 1 | Example 2 | Example 3 | Example 4 | Comparative Example 1 | Comparative Example 2 | Comparative Example 3 |
|---|---|---|---|---|---|---|---|---|
| | Substrate | ARTON, t 188 μm | ARTON, t 188 μm | Zeonor Film, t 188 μm | Zeonor Film, t 188 μm | PET film, t 188 μm | COP resin | COP resin |
| Resin Layer | Photopolymerizable monomer 1 | N-vinyl pyrolidone | Fluorine-containing acrylate | N-vinyl pyrolidone | N-vinyl pyrolidone | Fluorine-containing acrylate | Injection molding product t 400 μm | Injection molding product t 300 μm |
| | Photopolymerizable monomer 2 | | Trimethylol propane triacrylate | Trimethylol propane triacrylate | Trimethylol propane triacrylate | Trimethylol propane triacrylate | | |
| | Photopolymerizable oligomer | Urethane oligomer | Urethane oligomer | Urethane oligomer | Urethane oligomer | Urethane oligomer | | |
| | Photopolymerization initiator-1 | Omnirad 184 | Omnirad 184 | Omnirad 184 | Omnirad 184 | Omnirad 184 | | |

TABLE 1-continued

| Sample | | Example 1 | Example 2 | Example 3 | Example 4 | Comparative Example 1 | Comparative Example 2 | Comparative Example 3 |
|---|---|---|---|---|---|---|---|---|
| Photopolymerization initiator 2 | | | | | | Omnirad 369 | | |
| Parts by weight | | 50:50:05 | 17:50:50:5 | 33:47:20:5 | 33:57:10:5 | 17:50:50:5:2 | | |
| 350 nm~800 nm Maximum absorption coefficient | Substrate | 0.001 μm$^{-1}$ | 0.001 μm$^{-1}$ | 0.0002 μm$^{-1}$ | 0.0002 μm$^{-1}$ | 0.002 μm$^{-1}$ | | |
| | Resin layer | 0.005 μm$^{-1}$ | 0.008 μm$^{-1}$ | 0.003 μm$^{-1}$ | 0.0004 μm$^{-1}$ | 0.07 μm$^{-1}$ | | |
| 300 nm Absorption coefficient | Resin layer | 0.015 μm$^{-1}$ | 0.02 μm$^{-1}$ | 0.005 μm$^{-1}$ | 0.0007 μm$^{-1}$ | | | |
| Fs/Fb | | | 48 | | | 48 | | |
| Autofluorescence property Hoechst 33342 equivalent g | | 0.005 μg | 0.006 μg | 0.0025 μg | 0.001 μg | 0.22 μg | 0.01 μg | 0.004 μg |

In addition, the present invention is not limited to the above-mentioned Embodiment, and is capable of being carried into practice with various modifications. In the above-mentioned Embodiment, sizes, shapes and the like shown in the drawings are not limited thereto, and are capable of being modified as appropriate within the aspect for exerting the effects of the present invention.

According to this Embodiment, it is possible to provide the microwell film for bioassay that is a bioassay substrate which has the autofluorescence property lower than in the bioassay plate by conventional injection molding, is capable of being manufactured at low cost, is easy to perform temperature control of wells, is capable of suppressing the edge effect, and is applied to the "unimolecular enzyme assay" method and the like. Further, it is possible to provide the photosensitive resin composition capable of forming the microwell film for bioassay which is low in autofluorescence property and is easy to detect a marker, and the method of manufacturing the microwell film for bioassay using the photosensitive resin composition, and the present invention is readily applicable to uses in industry.

The present application is based on Japanese Patent Application No. 2019-123981 filed on Jul. 2, 2019, entire content of which is expressly incorporated by reference herein.

The invention claimed is:

1. A microwell film for bioassay, comprising:
at least a substrate; and
a resin layer having microwells on a surface thereof provided on one main surface of the substrate,
wherein in the substrate and the resin layer, an absorption coefficient at each of wavelengths of 350 nm to 800 nm is 0.01 μm$^{-1}$ or less.

2. The microwell film for bioassay according to claim 1, wherein an absorption coefficient of the resin layer at a wavelength of 300 nm is 0.02 μm$^{-1}$ or less, and is a maximum value among respective absorption coefficients at wavelengths of 300 nm to 800 nm.

3. The microwell film for bioassay according to claim 1, wherein the substrate and the resin layer contain nitrogen elements, an average nitrogen element concentration (Nf) of the resin layer is higher than an average nitrogen element concentration (Ns) of the substrate, and the substrate has a region with a nitrogen element concentration (Ni) meeting the following equation (1) on a first main surface side provided with the resin layer, $$Nf > Ni > Ns \qquad \text{Equation(1)}.$$

4. The microwell film for bioassay according to claim 1, wherein the resin layer is a cured material of a photosensitive resin composition derived from at least a photopolymerizable monomer and at least a photopolymerizable oligomer.

5. The microwell film for bioassay according to claim 4, wherein the resin layer is a cured material of a photosensitive resin composition containing at least a nitrogen-containing photopolymerizable monomer.

6. The microwell film for bioassay according to claim 1, wherein the substrate is polyethylene terephthalate, polycarbonate, cycloolefin polymer, polydimethylsiloxane or polystyrene.

7. The microwell film for bioassay according to claim 1, wherein in the resin layer, a ratio between a fluorine element concentration (Fs) of a surface of the resin layer and an average fluorine element concentration (Fb) in the resin layer meets the following equation (2, $$1 < Fs < Fb \leq 1500 \qquad \text{Equation(2)}.$$

8. A photosensitive resin composition for formation of a microwell film for bioassay, comprising:
(A) photopolymerizable monomer;
(B) photopolymerizable oligomer; and
(C) photopolymerization initiator,
wherein a content of the (A) photopolymerizable monomer is 10 to 80 percent by weight relative to weight of the photosensitive resin composition,
a content of the (B) photopolymerizable oligomer is 10 to 80 percent by weight relative to the weight of the photosensitive resin composition,
a content of the (C) photopolymerization initiator is 0.5 to 10.0 percent by weight relative to the weight of the photosensitive resin composition, and
an absorption coefficient at each of wavelengths of 350 nm to 800 nm after curing is 0.01 μm$^{-1}$ or less.

9. The photosensitive resin composition for formation of the microwell film for bioassay according to claim 8, wherein the (C) photopolymerization initiator is an α-hydroxyalkyl phenon-based polymerization initiator.

10. The photosensitive resin composition for formation of the microwell film for bioassay according to claim 8, wherein the (A) photopolymerizable monomer contains a nitrogen-containing photopolymerizable monomer.

11. The photosensitive resin composition for formation of the microwell film for bioassay according to claim 8, wherein the (A) photopolymerizable monomer contains a fluorine-containing (meth)acrylate expressed by the following chemical formula (1),

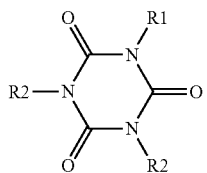

Chemical formula (1)

in the chemical formula (1), R1 represents the following chemical formula (2), and R2 represents the following chemical formula (3),

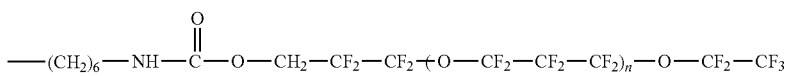

Chemical formula (2)

in the chemical formula (2), n is an integer ranging from "1" to "6",

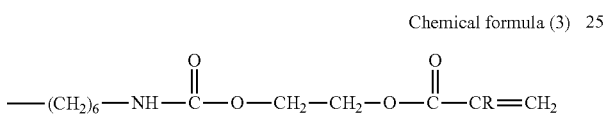

Chemical formula (3)

in the chemical formula (3), R represents H or $CH_3$.

12. A method of manufacturing the microwell film for bioassay according to claim 1, comprising the steps of:
applying onto at least a predetermined substrate or a master mold a photosensitive resin composition for formation of the microwell film for bioassay comprising:
(A) photopolymerizable monomer;
(B) photopolymerizable oligomer; and
(C) photopolymerization initiator,
wherein a content of the (A) photopolymerizable monomer is 10 to 80 percent by weight relative to weight of the photosensitive resin composition,
a content of the (B) photopolymerizable oligomer is 10 to 80 percent by weight relative to the weight of the photosensitive resin composition,
a content of the (C) photopolymerization initiator is 0.5 to 10.0 percent by weight relative to the weight of the photosensitive resin composition, and
an absorption coefficient at each of wavelengths of 350 nm to 800 nm after curing is 0.01 $\mu m-$ or less;
pressing the photosensitive resin composition between the substrate and the master mold;
curing the photosensitive resin composition by exposure to light to obtain a cured material; and
peeling off the cured material from the master mold.

13. A method of manufacturing the microwell film for bioassay according to claim 3, comprising:
applying onto at least a predetermined substrate a photosensitive resin composition for formation of the microwell film for bioassay, comprising:
(A) photopolymerizable monomer;
(B) photopolymerizable oligomer; and
(C) photopolymerization initiator,
wherein a content of the (A) photopolymerizable monomer is 10 to 80 percent by weight relative to weight of the photosensitive resin composition,
a content of the (B) photopolymerizable oligomer is 10 to 80 percent by weight relative to the weight of the photosensitive resin composition,
a content of the (C) photopolymerization initiator is 0.5 to 10.0 percent by weight relative to the weight of the photosensitive resin composition, and
an absorption coefficient at each of wavelengths of 350 nm to 800 nm after curing is 0.01 $\mu m^{-1}$ or less, wherein the (A) photopolymerizable monomer contains a nitrogen-containing photopolymerizable monomer,
leaving the substrate with the photosensitive composition applied thereon for a predetermined time after applying the photosensitive composition onto the substrate;
pressing the photosensitive resin composition between the substrate and a master mold;
curing the photosensitive resin composition by exposure to light to obtain a cured material; and
peeling off the cured material from the master mold.

14. A method of manufacturing the microwell film for bioassay according to claim 7, comprising the steps of:
applying onto at least a predetermined substrate or a master mold a photosensitive resin composition for formation of the microwell film for bioassay comprising:
(A) photopolymerizable monomer;
(B) photopolymerizable oligomer; and
(C) photopolymerization initiator,
wherein a content of the (A) photopolymerizable monomer is 10 to 80 percent by weight relative to weight of the photosensitive resin composition,
a content of the (B) photopolymerizable oligomer is 10 to 80 percent by weight relative to the weight of the photosensitive resin composition,
a content of the (C) photopolymerization initiator is 0.5 to 10.0 percent by weight relative to the weight of the photosensitive resin composition, and
an absorption coefficient at each of wavelengths of 350 nm to 800 nm after curing is 0.01 $\mu m^{-1}$ or less, wherein the (A) photopolymerizable monomer contains a fluorine-containing (meth)acrylate expressed by the following chemical formula (1),

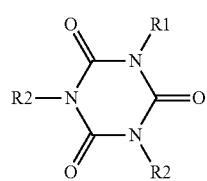

Chemical formula (1)

in the chemical formula (1), R1 represents the following chemical formula (2), and R2 represents the following chemical formula (3), Chemical formula (2)

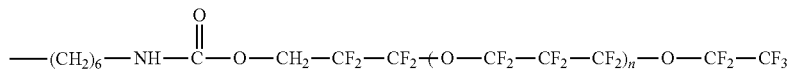

in the chemical formula (2), n is an integer ranging from "1" to "6",

Chemical formula (3)

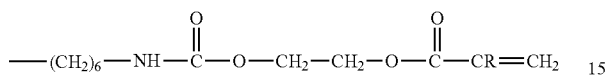

in the chemical formula (3), R represents H or $CH_3$;
  pressing the photosensitive resin composition between the substrate and the master mold;
  curing the photosensitive resin composition by exposure to light to obtain a cured material; and
  peeling off the cured material from the master mold.
  15. The microwell film for bioassay according to claim 1 which is suitable for use in a unimolecular enzyme assay method.

\* \* \* \* \*